: US009657261B2

United States Patent
Charest et al.

(10) Patent No.: US 9,657,261 B2
(45) Date of Patent: *May 23, 2017

(54) SYSTEMS, METHODS, AND DEVICES RELATING TO A BIOMIMETIC CELLULARIZED NEPHRON UNIT

(75) Inventors: Joseph L. Charest, Cambridge, MA (US); Else Frohlich, Brookline, MA (US); Jeffrey T. Borenstein, Newton, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/524,981

(22) Filed: Jun. 15, 2012

(65) Prior Publication Data

US 2012/0318726 A1 Dec. 20, 2012

Related U.S. Application Data

(60) Provisional application No. 61/497,854, filed on Jun. 16, 2011, provisional application No. 61/497,376, filed on Jun. 15, 2011.

(51) Int. Cl.
| | | |
|---|---|---|
| C12N 5/071 | (2010.01) | |
| C12M 3/00 | (2006.01) | |
| C12M 3/06 | (2006.01) | |
| A61M 1/14 | (2006.01) | |
| C12M 1/00 | (2006.01) | |
| C12M 1/12 | (2006.01) | |

(52) U.S. Cl.
CPC .............. *C12M 23/16* (2013.01); *A61M 1/14* (2013.01); *C12M 23/00* (2013.01); *C12M 23/06* (2013.01); *C12M 25/10* (2013.01); *C12M 29/04* (2013.01)

(58) Field of Classification Search
CPC ......... C12M 23/16; C12M 25/10; A61M 1/14
USPC ....................................................... 435/395
See application file for complete search history.

(56) References Cited

U.S. PATENT DOCUMENTS

| | | |
|---|---|---|
| 6,455,311 B1 | 9/2002 | Vacanti |
| 6,585,675 B1 | 7/2003 | O'Mahony et al. |
| 6,653,124 B1 | 11/2003 | Freeman |
| 6,653,142 B1 | 11/2003 | Opitz et al. |
| 6,942,879 B2 | 9/2005 | Humes |
| 7,264,723 B2 | 9/2007 | Singh et al. |

(Continued)

FOREIGN PATENT DOCUMENTS

| | | |
|---|---|---|
| CN | 101084054 A | 12/2007 |
| EP | 1 547 676 A1 | 6/2005 |

(Continued)

OTHER PUBLICATIONS

Goto et al., Micro- and nanometer-scale patterned surface in a microchannel for cell culture in microfluidic devices. Analytical and Bioanalytical Chemistry, vol. 390 (2008) pp. 817-823.*

(Continued)

*Primary Examiner* — Kara Johnson
(74) *Attorney, Agent, or Firm* — McDermott Will & Emery LLP

(57) ABSTRACT

Disclosed herein are systems and devices for culturing cells in a biomimetic environment of a cellularized nephron unit, and methods for fabricating and using the cellularized nephron unit.

33 Claims, 22 Drawing Sheets
(2 of 22 Drawing Sheet(s) Filed in Color)

(56) References Cited

U.S. PATENT DOCUMENTS

| | | | |
|---|---|---|---|
| 7,371,400 | B2 | 5/2008 | Borenstein et al. |
| 7,378,280 | B2 | 5/2008 | Quake et al. |
| 7,759,113 | B2 | 7/2010 | Vacanti et al. |
| 7,776,021 | B2 | 8/2010 | Borenstein et al. |
| 7,790,028 | B1 * | 9/2010 | Weinberg et al. ......... 210/321.6 |
| 7,790,443 | B2 | 9/2010 | Wikswo et al. |
| 7,955,504 | B1 | 6/2011 | Jovanovic et al. |
| 7,977,089 | B2 | 7/2011 | Wikswo et al. |
| 8,147,562 | B2 | 4/2012 | Vacanti et al. |
| 2001/0003653 | A1 | 6/2001 | Banes |
| 2002/0052571 | A1 | 5/2002 | Fazio |
| 2002/0182241 | A1 | 12/2002 | Borenstein et al. |
| 2003/0003575 | A1 | 1/2003 | Vacanti et al. |
| 2003/0119184 | A1 | 6/2003 | Humes |
| 2004/0077075 | A1 | 4/2004 | Jensen et al. |
| 2004/0084370 | A1 | 5/2004 | Singh et al. |
| 2004/0147032 | A1 | 7/2004 | Martin et al. |
| 2004/0265183 | A1 | 12/2004 | Sundararajan |
| 2005/0048519 | A1 | 3/2005 | Chien et al. |
| 2005/0202557 | A1 | 9/2005 | Borenstein et al. |
| 2005/0238687 | A1 | 10/2005 | Humes |
| 2006/0016685 | A1 | 1/2006 | Hawkins et al. |
| 2006/0136182 | A1 | 6/2006 | Vacanti et al. |
| 2007/0048727 | A1 | 3/2007 | Shuler et al. |
| 2007/0183935 | A1 | 8/2007 | Clemmens et al. |
| 2007/0266801 | A1 | 11/2007 | Khademhosseini et al. |
| 2007/0281353 | A1 | 12/2007 | Vacanti et al. |
| 2008/0026464 | A1 | 1/2008 | Borenstein et al. |
| 2008/0093298 | A1 | 4/2008 | Browning et al. |
| 2008/0251444 | A1 | 10/2008 | Fendya et al. |
| 2009/0101559 | A1 | 4/2009 | Bala Subramaniam et al. |
| 2009/0120864 | A1 | 5/2009 | Fulkerson et al. |
| 2009/0211977 | A1 | 8/2009 | Miller |
| 2009/0234332 | A1 | 9/2009 | Borenstein et al. |
| 2010/0086992 | A1 | 4/2010 | Himmelhaus et al. |
| 2011/0086427 | A1 * | 4/2011 | Faris et al. .................... 435/395 |
| 2011/0250585 | A1 | 10/2011 | Ingber et al. |
| 2011/0312569 | A1 | 12/2011 | Silverbrook et al. |

FOREIGN PATENT DOCUMENTS

| | | |
|---|---|---|
| GB | 2 262 538 A | 6/1993 |
| JP | H07-504570 | 5/1995 |
| JP | H09-501324 | 2/1997 |
| JP | 2005-143343 A | 6/2005 |
| JP | 2006-122012 | 5/2006 |
| JP | 2006-191809 | 7/2006 |
| JP | 2007020486 A | 2/2007 |
| JP | 2009-502446 A | 1/2009 |
| JP | 2009-055793 | 3/2009 |
| JP | 2011-000040 | 1/2011 |
| WO | WO-95/11048 | 4/1995 |
| WO | WO-95/24464 A1 | 9/1995 |
| WO | WO-97/05238 A1 | 2/1997 |
| WO | WO-02/076529 A1 | 10/2002 |
| WO | WO-2006/037033 A2 | 4/2006 |
| WO | WO-2006/112709 A2 | 10/2006 |
| WO | WO-2008/100559 | 8/2008 |
| WO | WO-2008/153783 A1 | 12/2008 |
| WO | WO-2009/102751 A2 | 8/2009 |
| WO | WO-2010/009307 A2 | 1/2010 |
| WO | 2010115167 A2 | 4/2010 |
| WO | WO-2010/124227 A2 | 10/2010 |
| WO | 2011044117 A2 | 4/2011 |
| WO | WO-2011/040889 | 4/2011 |
| WO | WO-2011/044117 | 4/2011 |

OTHER PUBLICATIONS

Chung et al., Nanopatterned interfaces for controlling cell behavior. Nano Life, vol. 1 (Mar. & Jun. 2010) pp. 63-77.*

Rebollar et al., Proliferation of aligned mammalian cells on laser-nanostructured polystyrene. Biomaterials, vol. 29 (2008) pp. 1796-1806.*

Bourgeois et al., "Differentiated thick ascending limb (TAL) cultured cells derived from SV40 transgenic mice express functional apical NHE2 isoform: effect of nitric oxide," Eur. J. Phvsiol., 446:672-683 (2003).

Clark P et al: "Topographical Control of Cell Behaviour: I. Simple Step Cues", Development, Company of Biologists, Cambridge, GB, vol. 99, No. 3, Mar. 1, 1987, pp. 439-448, ISSN: 0950-1991.

Clark P et al: "Topographical Control of Cell Behaviour: II. Multiple Grooved Substrata", Development, Company of Biologists, Cambridge, GB, vol. 108, Jan. 1, 1990, pp. 635-644, ISSN: 0950-1991.

Final Office Action in U.S. Appl. No. 12/915,259 dated Sep. 11, 2013.

International Preliminary Report on Patentability Issued on May 10, 2012 in PCT Appl. PCT/US2010/054602.

International Search Report and Written Opinion issued Aug. 30, 2012 in PCT Application No. PCT/US2012/042769.

International Search Report and Written Opinion issued Sep. 4, 2012 in PCT Application No. PCT/US2012/042791.

International Search Report in PCT/US2010/054602 dated Dec. 27, 2010.

International Search Report, International application No. PCT/US2013/028879, mailed May 17, 2013.

Office Action in U.S. Appl. No. 12/915,259 dated Jan. 3, 2013.

Office Action in U.S. Appl. No. 13/525,085 dated Apr. 3, 2013.

Schumacher et al., "Advanced technique for long term culture of epithelia in a continuous luminal-basal medium gradient," Biomaterials, 23:805-815 (2002).

US Office Action in U.S. Appl. No. 13/161,963 DTD Oct. 1, 2012.

US Office Action in U.S. Appl. No. 13/161,963 DTD Mar. 27, 2012.

Weinberg et al., "Concept and computational design for a bioartificial nephron-on-a-chip," International Journal of Artificial Organs, vol. 31, No. 6, Jun. 1, 2008, pp. 508-514.

Zhang et al., "Proliferation and osmotic tolerance of renal inner medullary epithelial cells in vivo and in cell culture," Am. J. Phvsiol Renal Phvsiol., 283: F302-F308 (2002).

Office Action issued Dec. 9, 2013 in Chinese Patent Application No. 201080048990.6 (9 pages).

Pries, et al., "Blood flow in microvascular networks. Experiments and simulation." Circ Res. 1990; 67: 826-834.

US Office Action in U.S. Appl. No. 13/525,085 DTD Dec. 4, 2013.

US Office Action in U.S. Appl. No. 12/915,259 DTD Jan. 13, 2014.

Japanese Office Action mailed Aug. 13, 2014 in Japanese Patent Application No. 2012-537090, 13 pages (with translation).

Supplementary European Search Report mailed Aug. 7, 2014 in European Patent Application 10830479(6 pages).

US Office Action in U.S. Appl. No. 12/915,259 DTD Sep. 2, 2014.

Weinberg, E. Concept and computational design for a bioartificial nephron-on-a-chip, The International Journal of Artificial Organs, Wichtig Publishing, vol. 31, pp. 508-514 (2008).

Chinese Office Action mailed Aug. 13, 2014 in CN Patent Application No. 201080048990.6.

First Office Action issued Nov. 13, 2014 in Chinese Patent Application No. 2012800372037.

International Preliminary Report on Patentability mailed Sep. 12, 2014 in PCT Application No. PCT/US2013/028879.

Makiko Goto, et al. Micro- and nanometer-scale patterned surface in a microchannel for cell culture in microfluidic devices, Anal Bioanal Chem. vol. 390, Issue 3, pp. 817-823, Feb. 28, 2008.

Office Action issued Dec. 12, 2014 in Australian Patent Application No. 2010319881.

US Office Action in U.S. Appl. No. 13/525,085 DTD Jan. 5, 2015.

US Office Action in U.S. Appl. No. 13/784,271 DTD Apr. 10, 2015.

Notice of Reason for Rejection issued Mar. 3, 2016 in Japanese Patent Application No. 2014-416054.

Patent Examination Report No. 1 in Australian Patent Application No. 2012271412, dated Jan. 27, 2016.

Third Office Action issued in Chinese Patent Application No. 201280037203.7, mailed on Feb. 15, 2016.

First Office Action dated Jul. 3, 2015 in Chinese Patent Application No. 201280037209.4.

Further Examination Report issued Nov. 18, 2015 in European Patent Application No. 10830479.1.

(56) References Cited

OTHER PUBLICATIONS

Office Action issued Jun. 1, 2015 in Japanese Patent Application No. 2012-537090.
Office Action issued Jun. 9, 2015 in European Patent Application No. 10830479.1.
Second Office Action dated Jul. 17, 2015 in Chinese Patent Application No. 201280037203.7.
US Office Action in U.S. Appl. No. 13/784,271 DTD Sep. 11, 2015.
US Office Action on U.S. Appl. No. 13/525,085 DTD Aug. 31, 2015.
US Office Action on U.S. Appl. No. 14/588,770 DTD Dec. 1, 2015.
Patent Examination Report No. 1, issued Jun. 26, 2016 in Australian Patent Application No. 2012271341 (3 pages).
Second Office Action issued May 5, 2016 in Chinese Patent Application No. 201280037209.4 (14 pages).
Fourth Office Action issued Aug. 17, 2016 in Chinese Patent Application No. 201280037203.7 (31 pages).
Office Action issued Oct. 5, 2016 in European Patent Application No. 12737373.6 (5 pages).
Rejection issued Apr. 21, 2016 in Japanese Patent Application No. 2014-516061 (6 pages).
Office Action issued Apr. 6, 2016 in U.S. Appl. No. 13/525,085 (34 pages).
Office Action issued Sep. 6, 2016 in U.S. Appl. No. 13/784,271 (15 pages).
Patent Examination Report No. 1, issued Oct. 25, 2016 in Australian Patent Application No. 2013225681 (3 pages).
Office Action issued Jun. 2, 2016 in U.S. Appl. No. 14/588,770 (18 pages).
Office Action issued Sep. 16, 2016 in U.S. Appl. No. 14/588,770 (22 pages).
Office Action issued Sep. 19, 2016 in European Patent Application No. 12732900.1 (4 pages).
Office Action issued Nov. 23, 2016 in U.S. Appl. No. 13/525,085.
Office Action issued Dec. 23, 2016 in U.S. Appl. No. 13/784,271.
Third Office Action issued Jan. 3, 2017 in Chinese Patent Application No. 201280037209.4.
Office Action issued Sep. 28, 2016 in Canadian Patent Application No. 2,778,247.
Office Action issued Dec. 14, 2016 in Japanese Patent Application No. 2014-560128.
Office Action issued Jan. 6, 2017 in Chinese Patent Application No. 201280037203.7.
Office Action issued Jan. 16, 2017 in Japanese Patent Application No. 2014-516054.
Office Action issued Jan. 26, 2017 in European Patent Application No. 13710243.0.
Office Action issued Feb. 16, 2017 in European Patent Application No. 12732900.1.

\* cited by examiner

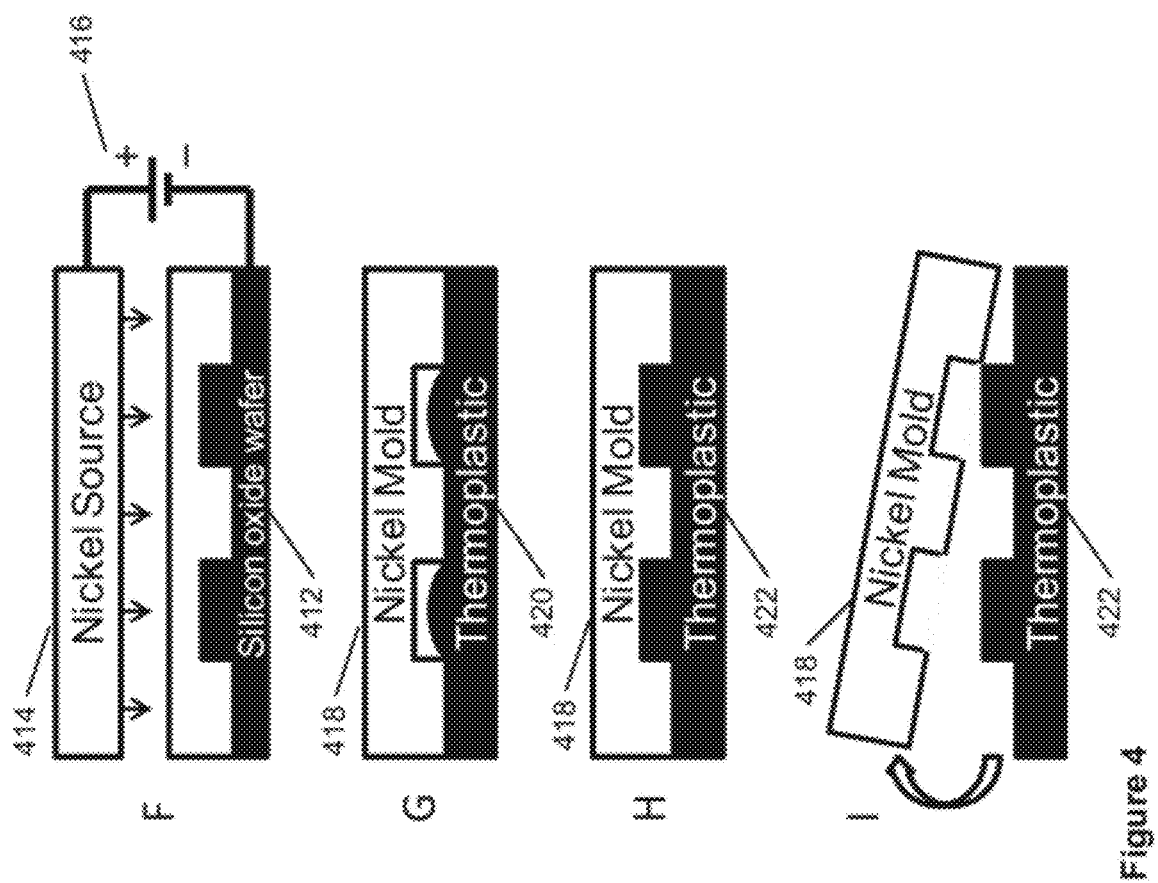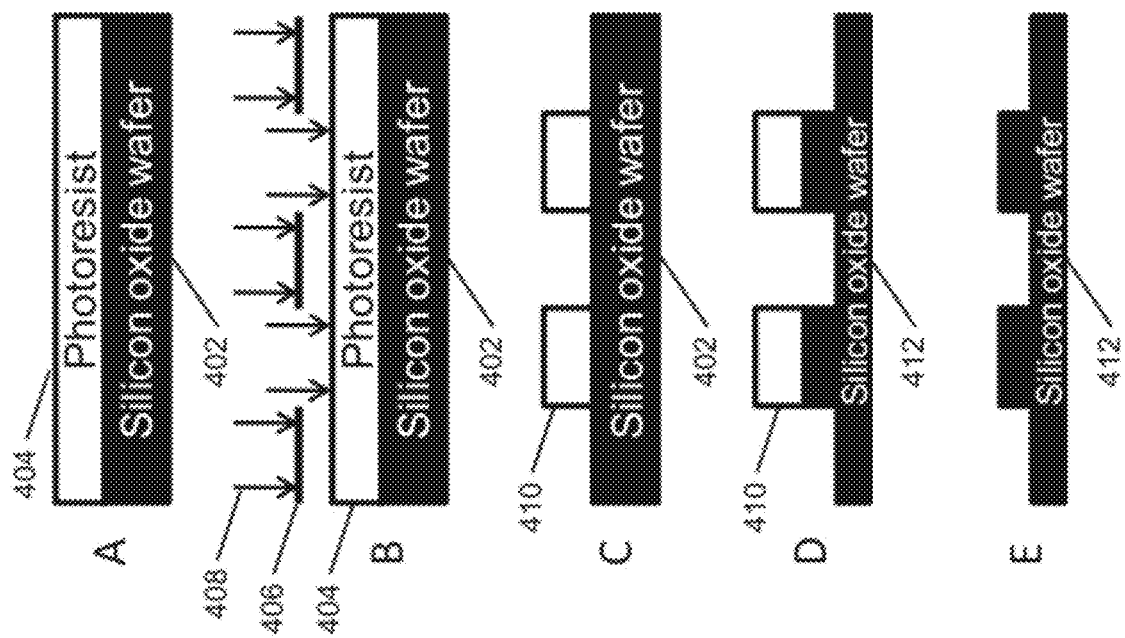
Figure 4

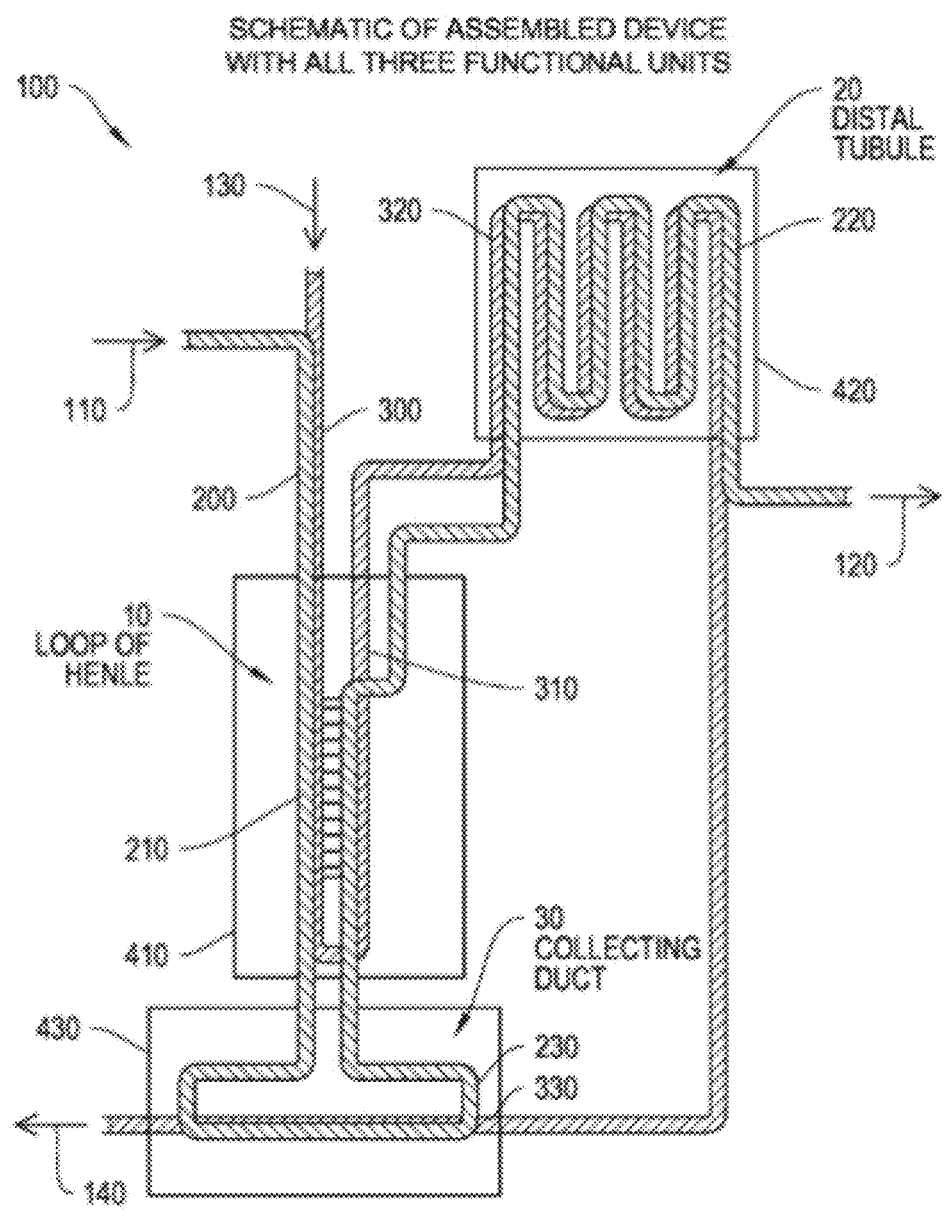

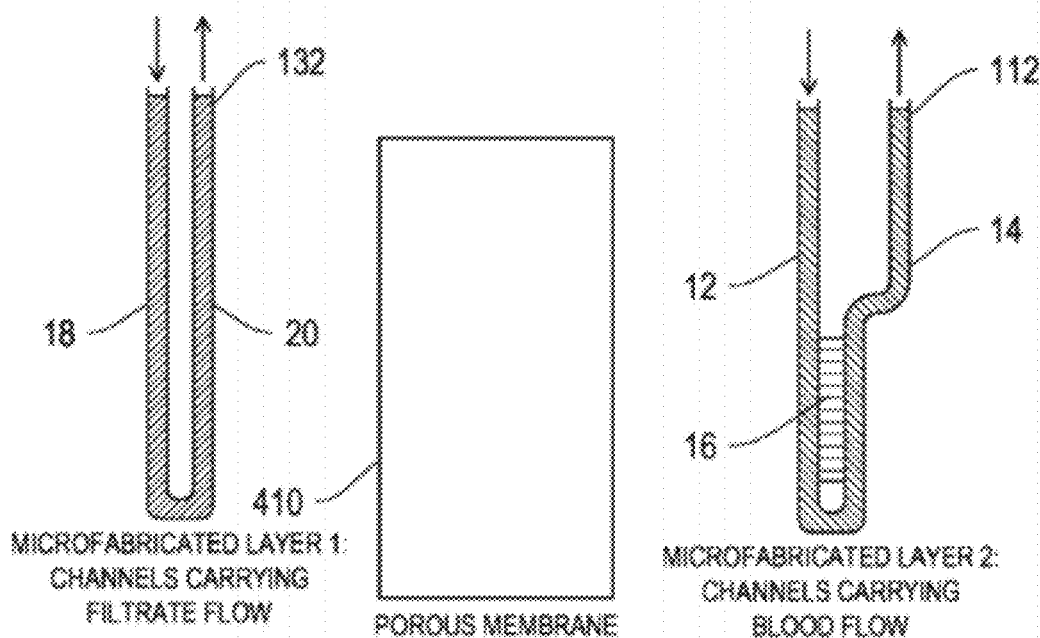

SCHEMATIC OF ASSEMBLED LAYERS OF MICROFABRICATED LOOP OF HENLE: BLOOD LAYER ON TOP OF MEMBRANE, FILTRATE LAYER BELOW AND SHOWING THROUGH THE MEMBRANE

SCHEMATIC OF CELLS SEEDED IN FILTRATE LAYER

Figure 17
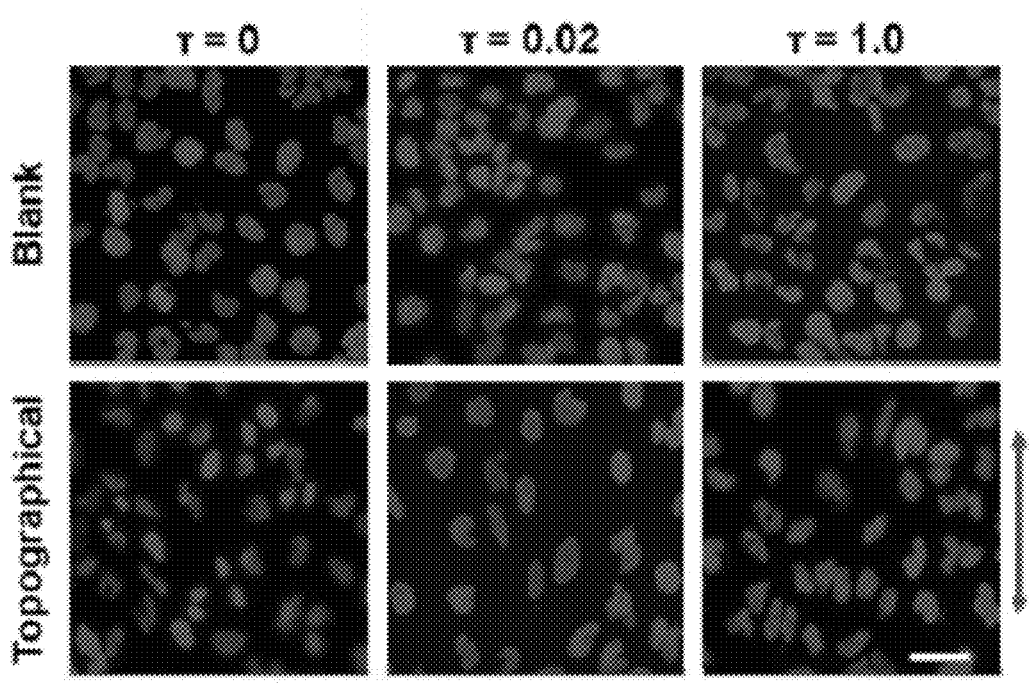
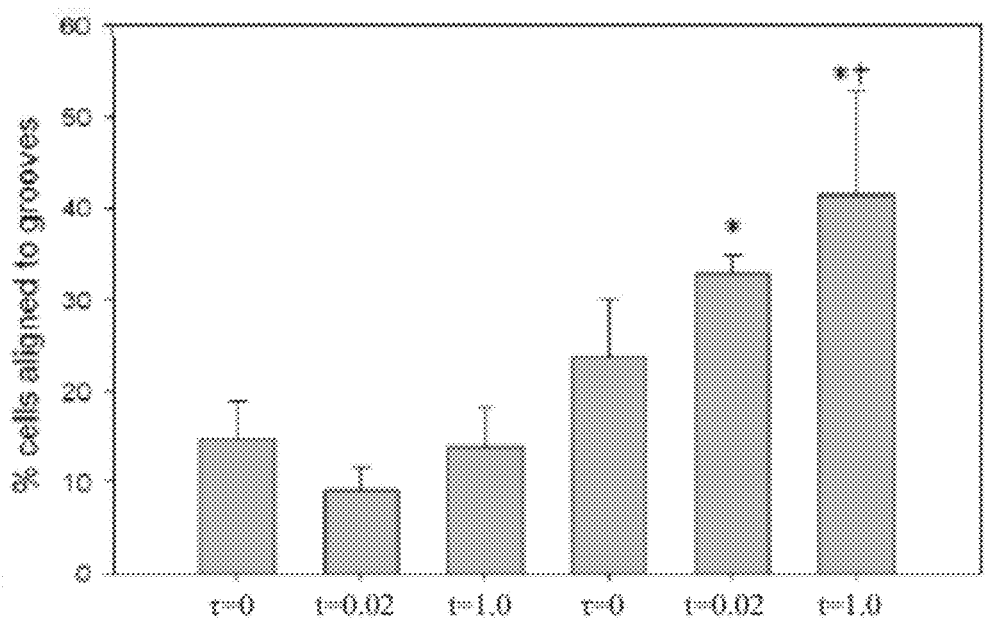

Figure 18
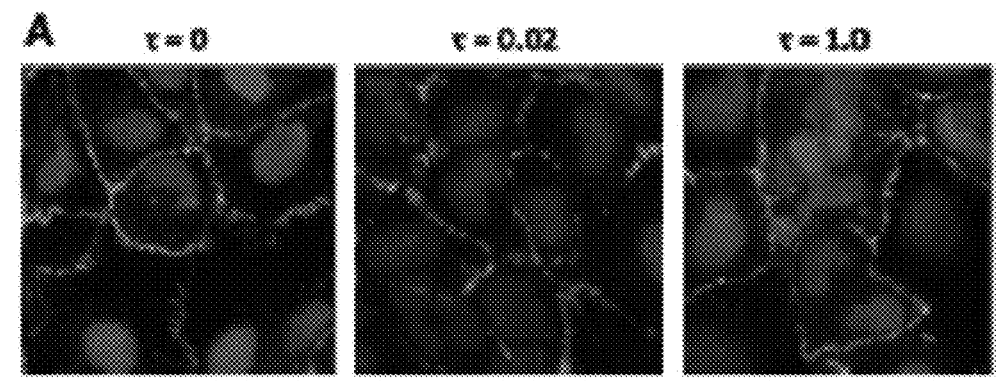
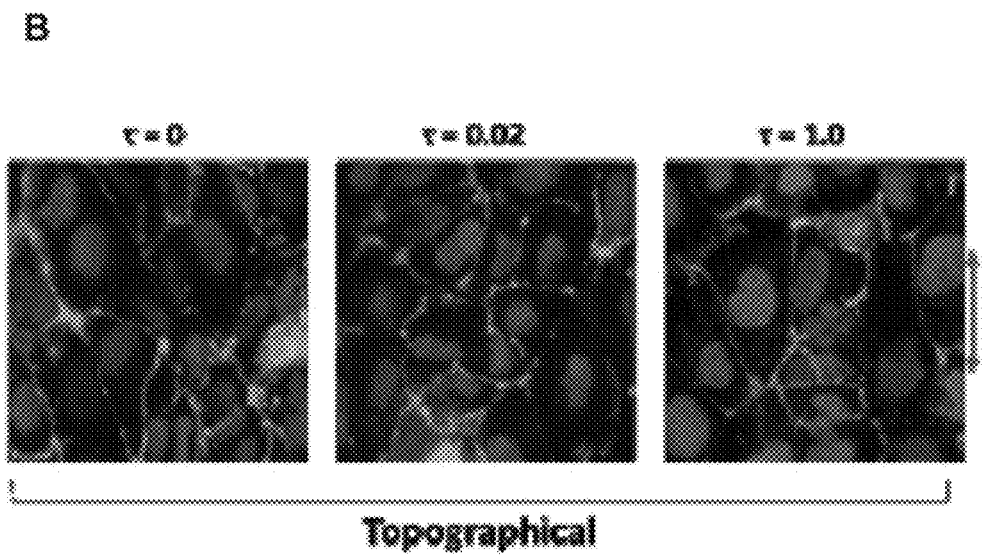

Figure 19
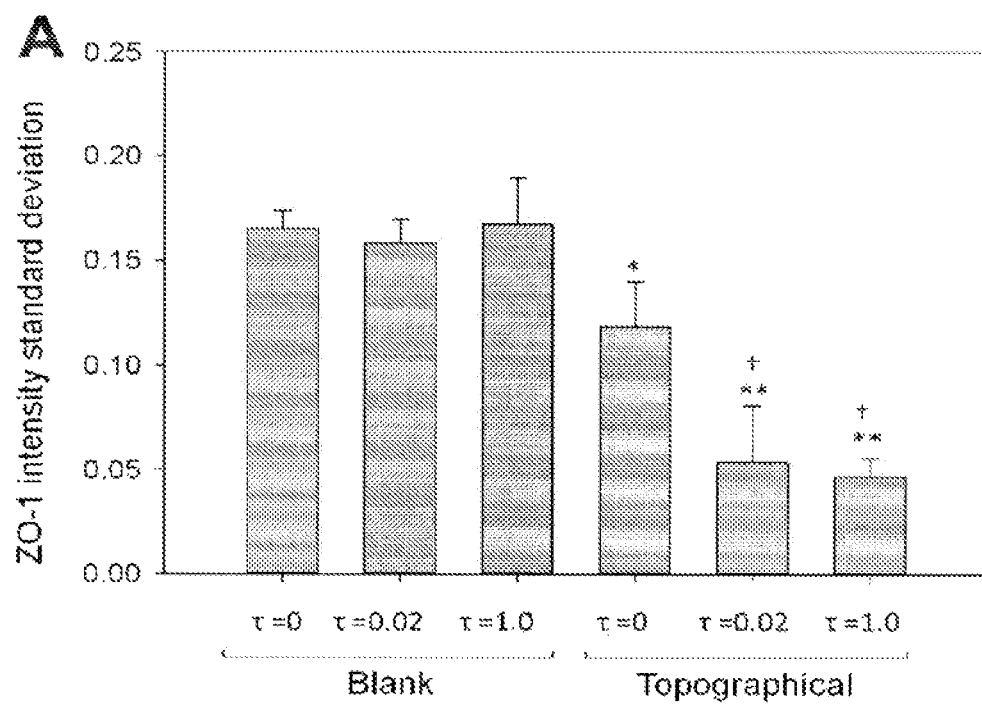
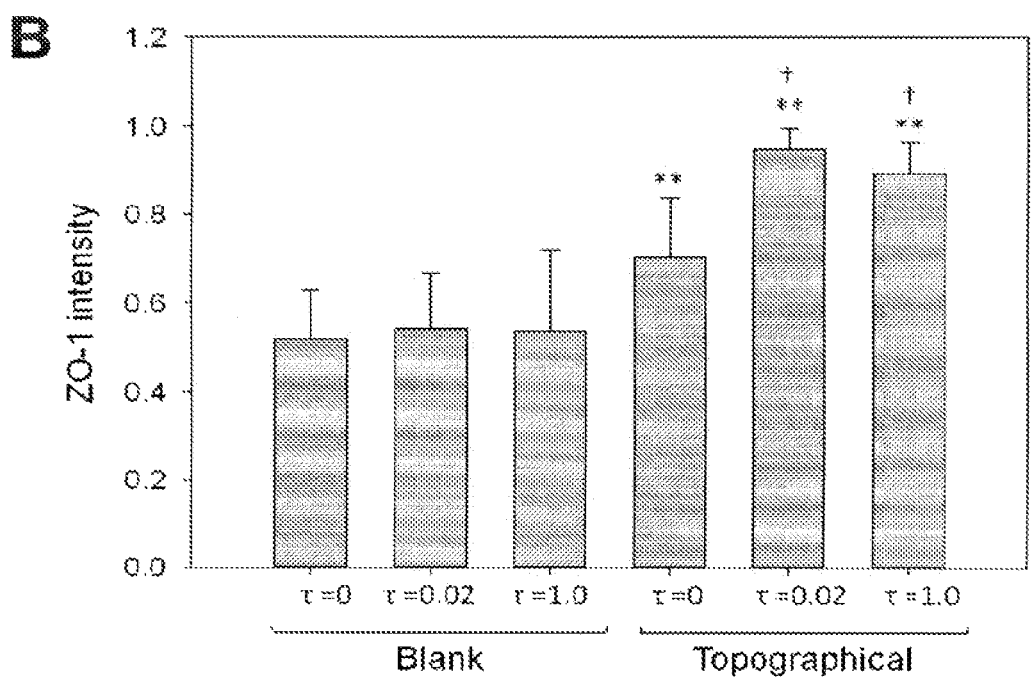

SYSTEMS, METHODS, AND DEVICES RELATING TO A BIOMIMETIC CELLULARIZED NEPHRON UNIT

RELATED PATENTS AND APPLICATIONS

This Application claims the benefit of U.S. Provisional Application No. 61/497,376, filed on Jun. 15, 2011, and U.S. Provisional Application No. 61/497,854, filed on Jun. 16, 2011, which are incorporated herein by reference in their entirety.

FIELD

In general, the disclosure relates to a systems and devices for culturing cells in a biomimetic environment of a cellularized nephron unit and a method for fabricating and using the cellularized nephron unit.

BACKGROUND

Kidney cells grown under controlled in vitro conditions have a wide range of potential applications in the study of kidney functionality, the production of medical devices, and the testing of pharmaceuticals. Kidney cell cultures allow biologists to study the functions of kidney-related cells and observe cells' responses to various conditions. Highly controlled nephritic environments can be used to perform some functions of the kidney to assist a patient with renal disease, and could be used by tissue engineers to generate specific kidney tissues for implantation into a patient with renal disease. Furthermore, kidney cell cultures can be used in the development of pharmaceuticals for kidney therapy and for testing kidney toxicity of pharmaceuticals. A controlled in vitro environment can be used for other types of cells as well, such as for eliciting desired cell functions of stem cells.

Each of these applications is benefited by conditions that cause the in vitro cells to accurately replicate cells in vivo. While devices and methods exist for culturing kidney cells, traditional in vitro kidney cell environments are static, failing to account for shear stress experienced in nephrons. Furthermore, previous in vitro environments for kidney cell cultures do not provide biomimetic cues such as those provided by the extracellular matrix (ECM), so cells grown in the previous environments do not have the phenotype and morphology, for example cell shape or arrangement, they have in vivo. Proper arrangement of kidney cells in nephrons, particularly the formation of cell-to-cell junctions between cells, is necessary for kidney cells to perform their filtering and absorption functions. Thus, kidney cells grown in previous apparatuses fail to mimic the conditions of a nephron.

SUMMARY

There is therefore a need for biomimetic device that can be used to grow a kidney cell culture that better replicates in vivo conditions of a nephron. In particular, an apparatus that controls the geometry and arrangement of cells in a flow channel can be used to create an in vitro environment that more closely mimics in vivo conditions than previous apparatuses. Microfabrication and micromolding techniques can be used to produce artificial cellular substrates with micro-, sub-micro-, and nano-topographical patterns that mimic the effect the extracellular matrix (ECM) has upon kidney cells. The design of the topographical surface allows close control of cells grown atop the substrate. This surface patterning, along with additional flow channel parameters such as channel height, channel cross-sectional area, and flow rate, can be used to create highly controlled in vitro conditions that closely mimic the in vivo environment of specific cell types.

Accordingly, in some aspects, disclosed herein are devices and methods for constructing and utilizing artificial organs, such as bioartificial kidneys. In some embodiments, a bioartificial kidney of the present technology includes a microfluidic flow channel comprising at least one topographical surface; an inlet in fluid connection with the flow channel for allowing fluid to flow into the flow channel; and renal cells seeded on the topographical surface, wherein the topography of the surface of the flow channel is selected to cause the renal cells to form a cell layer disposed above the surface to achieve an arrangement, behavior, or morphology determined at least in part by the topography of the at least one surface. Additionally or alternatively, in some embodiments, the topography of the surface is selected to promote increased adhesion of cells in the cell layer to the at least one surface. Additionally or alternatively, in some embodiments, the surface topography causes the arrangement, behavior, or morphology of the cell layer to replicate an arrangement, behavior, or morphology of cells in a kidney.

In some embodiments, the flow channel is formed in the bioartificial kidney. In some embodiments, the flow channel is formed as part of one or more structures selected from the group consisting of a Loop of Henle, a collecting tubule and a distal tubule.

In some embodiments, the bioartificial kidney of the present technology includes a fluid source for flowing a fluid through the flow channel via the inlet, wherein the fluid induces a shear stress upon the cell layer. In some embodiments, the fluid source is configured to flow the fluid at a flow rate that results in a level of shear stress on the cell layer that is about 10.0 dyne/cm$^2$ in at least one region of the bioartificial kidney. In some embodiments, the shear stress is less than or equal to about 1.0 dyne/cm$^2$ in at least one region of the bioartificial kidney; in other embodiments the shear stress is less than or equal to about 0.1 dyne/cm$^2$ in at least one region of the bioartificial kidney; in still other embodiments, the shear stress is less than or equal to about 0.02 dyne/cm$^2$ in at least one region of the bioartificial kidney.

Additionally or alternatively, in some embodiments, the flow channel is configured to such that the fluid flows at a first flow rate in a first region of the bioartificial kidney and at a second flow rate in a second region of the bioartificial kidney. In some embodiments, the first flow rate results in a first level of shear stress on the cell layer in the first region, and the second flow rate results in a second level of shear stress on the cell layer in the second region. In some embodiments, the first and second level of shear stress are different. Different regions of the bioartificial kidney exposed to the different shear stress levels may include any structure of the device which includes a cell layer. By way of example but not by way of limitation, in some embodiments, the bioartificial kidney includes one or more of a collecting duct, a distal tubule and a Loop of Henle comprising an ascending and a descending limb. In some embodiments, the first region is the ascending limb of the Loop of Henle, and the second region is the descending limb of the Loop of Henle. In some embodiments, the first region is the Loop of Henle, and the second region is one or more of a collecting duct and a distal tubule.

Additionally or alternatively, in some embodiments, the channel is shaped such that flowing the fluid through the flow channel results in a plurality of shear stress values along a length of the flow channel. In some embodiments, the at least one surface of the flow channel has at least two different topographies. In some embodiments, the first surface of the flow channel has a first topography, and a second surface of the flow channel has a second topography. Different regions of the bioartificial kidney exhibiting different topography may include any structure of the device which will include a cell layer. By way of example but not by way of limitation, in some embodiments, the bioartificial kidney includes one or more of a collecting duct, a distal tubule and a Loop of Henle comprising an ascending and a descending limb. In some embodiments, the first surface is in the ascending limb of the Loop of Henle, and the second surface is in the descending limb of the Loop of Henle. In some embodiments, the first surface is in the Loop of Henle, and the second surface is in one or more of a collecting duct and a distal tubule. In some embodiments, the artificial kidney includes a transition topography surface between the first and second surface.

In some embodiments, the topography of the first surface comprises ridges with a first pitch, and the topography of the second surface comprises ridges with a second pitch. In some embodiments, the topography of the first surface comprises ridges in a first orientation with respect to fluid flow, and the topography of the second surface comprises ridges in a second orientation with respect to fluid flow. In some embodiments, first topography comprises ridges, and the second topography comprises one or more topographies of the pit and post family. In some embodiments, the topography of the surface comprises ridges having a width of about 5 μm or less.

In some embodiments, the bioartificial kidney includes a cytophilic substance, such as collagen, disposed on a portion of a substrate for growing the cell layer in the portion of the substrate. In some embodiments, the portion of the substrate forms a surface of the flow channel.

In some embodiments, the bioartificial kidney includes at least a second flow channel having at least one surface of the second flow channel having a topography formed therein. In some embodiments, the first flow channel is separated from the second flow channel by a membrane. In some embodiments, the first flow channel is seeded with renal epithelial cells; additionally or alternatively, in some embodiments, the second flow channel is seeded with vascular epithelial cells. In some embodiments, the first flow channel comprises a blood flow layer, and the second flow channel comprises a filtrate layer.

In some embodiments, at least one surface of the first channel includes a different surface topography than a corresponding surface in the second channel. For example, in some embodiments, the first channel surface topography comprises a different pitch or shape than the second channel surface topography. In some embodiments, the artificial kidney includes a first fluid source for flowing a fluid through the first flow channel and the second flow channel, wherein the fluid induces a first shear stress upon the cell layer in the first channel and a second shear stress upon the cell layer in the second flow channel. In some embodiments, the first shear stress is different than second shear stress.

In some embodiments, the renal cells seeded in the artificial kidney include one or more cell types selected from the group consisting of proximal tubule cells, renal proximal tubule epithelial cells, Madin-Darby canine kidney cells, primary inner medullary collecting duct cells, primary proximal tubule cells, embryonic stem-cells, adult stem-cells, induced pluripotent stem cells and endothelial cells.

BRIEF DESCRIPTION OF THE DRAWINGS

The application file contains at least one drawing executed in color. Copies of this patent application publication with color drawing(s) will be provided by the Office upon request and payment of the necessary fee.

The system and method may be better understood from the following illustrative description with reference to the following drawings in which:

FIGS. 4A-4I are a series of diagrams illustrating a method for producing a substrate with topographical patterning, according to an illustrative embodiment of the invention;

FIG. 10 is a schematic of an assembled integrated device including a microfabricated bioartificial Loop of Henle, distal tubule and collecting duct, comprising topographical structures for stimulating patterned cell growth, according to an illustrative embodiment of the invention;

FIG. 11 is a schematic of unassembled layers of a microfabricated bioartificial Loop of Henle comprising topographical structures for stimulating patterned cell growth, according to an illustrative embodiment of the invention;

FIG. 17A shows fluorescently-labeled nuclei of confluent layers of HK-2 cells grown on either blank (top row) or topographical (bottom row) substrates exposed to 2 hours of either 0, 0.02 or 1.0 dyne/cm$^2$ FSS. The arrow indicates the direction of grooves on the topographical substrate;

FIG. 17B is a bar graph showing the percent cells aligned to grooves. The first three bars represent cells grown on a blank substrate (no topography) and exposed to 0, 0.02 or 1 dyne/cm$^2$ FSS, respectively. The second three bars represent cells grown on a topographical substrate and exposed to 0, 0.02 or 1 dyne/cm$^2$ FSS, respectively;

FIGS. 18A and 18B show representative images of ZO-1 expression for cells cultured on blank or topographical substrates and exposed to either 0, 0.02 or 1 dyne/cm$^2$ FSS;

FIG. 19A is a bar graph showing ZO-1 intensity integrated along cell perimeters and normalized by cell perimeter. The first three bars represent cells grown on a blank substrate (no topography) and exposed to 0, 0.02 or 1 dyne/cm$^2$ FSS, respectively. The second three bars represent cells grown on a topographical substrate and exposed to 0, 0.02 or 1 dyne/cm$^2$ FSS, respectively;

FIG. 19B is a bar graph showing standard deviation of ZO-1 intensity measured along cell perimeters. The first three bars represent cells grown on blank substrate (no topography) and exposed to 0, 0.02 or 1 dyne/cm$^2$ FSS, respectively. The second three bars represent cells grown on topographical substrate and exposed to 0, 0.02 or 1 dyne/cm$^2$ FSS, respectively.

DETAILED DESCRIPTION

To provide an overall understanding of the invention, certain illustrative embodiments will now be described, including apparatuses and methods for culturing cells in a biomimetic environment. However, it will be understood by one of ordinary skill in the art that the systems and methods described herein may be adapted and modified as is appropriate for the application being addressed and that the systems and methods described herein may be employed in other suitable applications, and that such other additions and modifications will not depart from the scope thereof.

A biomimetic flow apparatus includes a flow channel having a fluid inlet and a fluid outlet. To create a flow channel that replicates an organ structure, such as a nephron, a culture of the organ's cells is grown on at least one side of the flow channel. In the body, the extracellular matrix (ECM) structurally supports the cells of a nephron and causes the cells lining a nephron to align with each other in a particular arrangement. In a biomimetic flow channel, the proper choice of topography for the surface upon which the cells are grown causes the cells to have the alignment and/or arrangement that would be created by the ECM. A biomimetic flow channel with a topography can be used to replicate not only kidney structures, but also parts of the bladder, digestive system, heart, veins, arteries, capillaries, lymphatic system, or any other structure which experiences fluid flow.

The effect of an exemplary surface topography on kidney cells is shown in FIG. 1. FIGS. 1A and 1B show two diagrams of kidney cell cultures. FIGS. 1C and 1D show two photographs taken of kidney cell cultures. FIG. 1A is a diagram of a culture of kidney cells 102 grown on a flat surface 104, such as a typical culture plate, dish, or flask. Traditionally, kidney cells are cultured in a fluid static state, experiencing no shear stress or topography. Even if the kidney cells experienced fluid flow and shear stress, the cells would not align and their morphology may not be affected. As seen in FIG. 1A, typical cultured kidney cells 102 do not have a characteristic shape or alignment, but rather appear randomly aligned. Additionally, the cells 102 do not form superstructures and are not typically joined to each other. FIG. 1C is a photograph of a culture of kidney cells gown on a flat surface 104. FIG. 1C illustrates how the cells 102 lack a characteristic shape and align randomly.

Figure 1A:
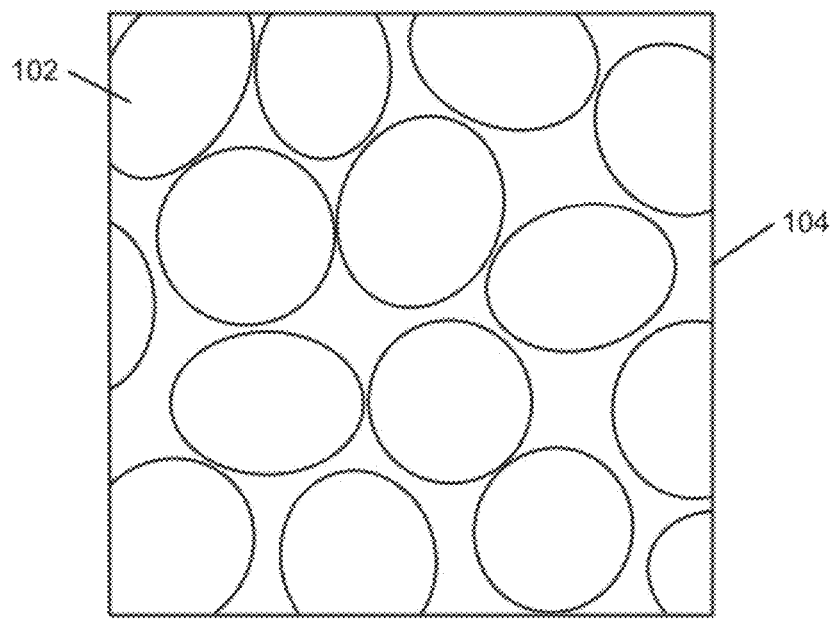
FIG. 1A is a diagram of a kidney cell culture grown on a flat surface.
Figure 1B:
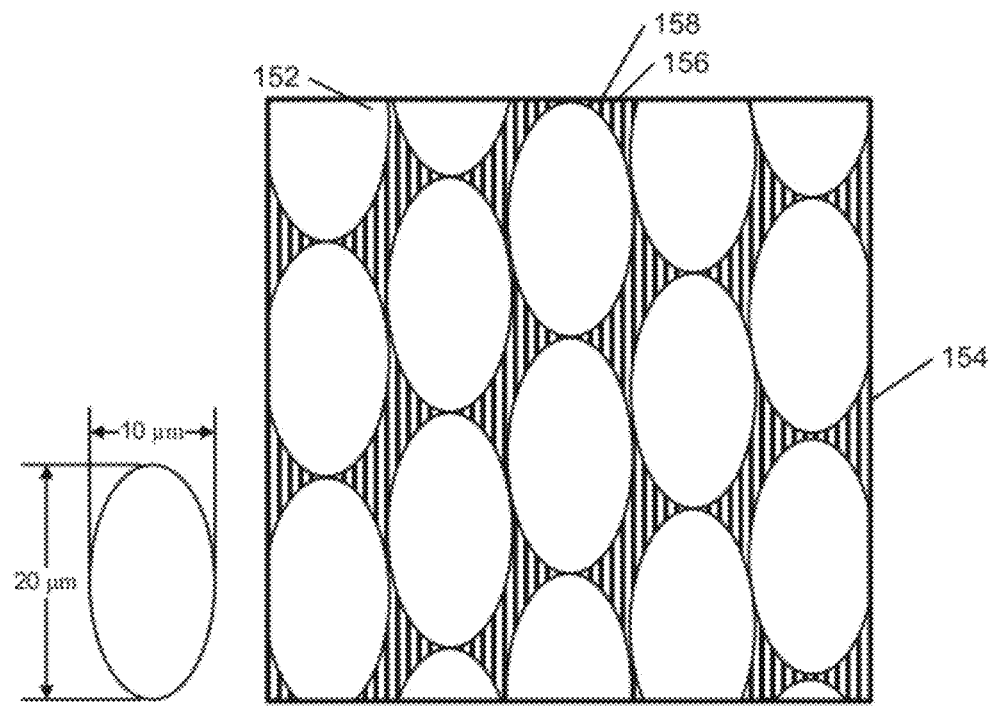
FIG. 1B is a diagram of a kidney cell culture grown on a substrate with topographical patterning, according to an illustrative embodiment of the invention.
Figure 1C:
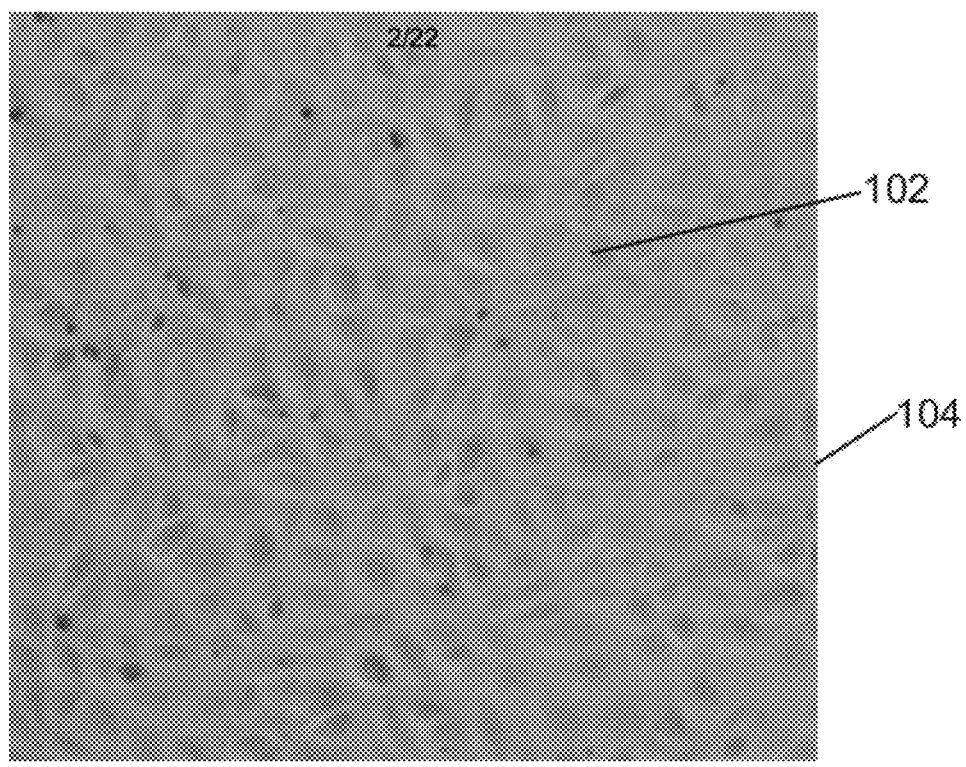
FIG. 1C is a picture of a kidney cell culture grown on a flat surface.

FIG. 1B is a diagram of a culture of kidney cells 152 grown on a surface 154 with an exemplary topographical pattern. The surface has grooves 156 and ridges 158 that are narrower than the cells 152. Each cell 152 straddles several grooves 156 and ridges 158. This pattern of grooves and ridges, like the extracellular matrix (ECM), causes the kidney cells 152 to lengthen and align themselves parallel to the ridges, encourages cell-to-cell junctions, and promotes the adhesion of the cells 152 to the surface 154. The scale given on the left gives approximate dimensions for some epithelial cells of the kidney; however, the actual sizes of kidney cells vary widely throughout the nephron. The morphology of the cells 152 is also exemplary; some types of kidney cells, particularly columnar cells, are more rectangular. In FIG. 1B, the grooves 156 and ridges 158 are approximately the same width, although they do not have to be. For a kidney cell with an elongated width of about 10 mm such as the cells 152, the width of the grooves 156 and ridges 158 should be about 5 mm or less so that the elongated cell is in contact with more than one ridge. In FIG. 1B, the widths of the grooves 156 and ridges 158 are about 800 nm. The grooves 156 and ridges 158 may be narrower than this, but if they are narrower than about 20 nm, the texture would have limited effect on kidney cells. The sizing of the topographical pattern depends on the size of the cells, however. Furthermore, for certain applications, it is desirable to have wider grooves in relation to the cell width so that the cells rest in the grooves. In such an embodiment, the ridges may be narrower than the grooves. In other embodiments, the ridges may be wider than the grooves.

In addition to controlling the orientation and shape of the cells, the grooves and ridges also cause the kidney cells 152 to join together and form more defined and well-developed junctions as compared to cells grown on a non-textured or "blank" substrate for the same period of time. The tight cell junction observed in vivo is necessary for nephrons to filter blood and reabsorb water properly. The tight junctions prevent fluid, including liquid and dissolved solutes, from passing in between cells, so fluids exiting the walls of the nephron must pass through the epithelial cells, which can control which fluids and/or solutes are passed. These cell junctions also will form in an in vitro environment when a surface topography, such as the grooves 156 and ridges 158, causes confluent cells to align so that their membranes can join to form this fluid-impermeable barrier. Flow channels can be arranged in any direction in relation to the surface 154 to cause fluid to flow in any direction over the cells 152. In embodiments shown in FIG. 6, fluid is flowed either parallel or perpendicular to the grooves 156 and ridges 158.

Figure 1D:
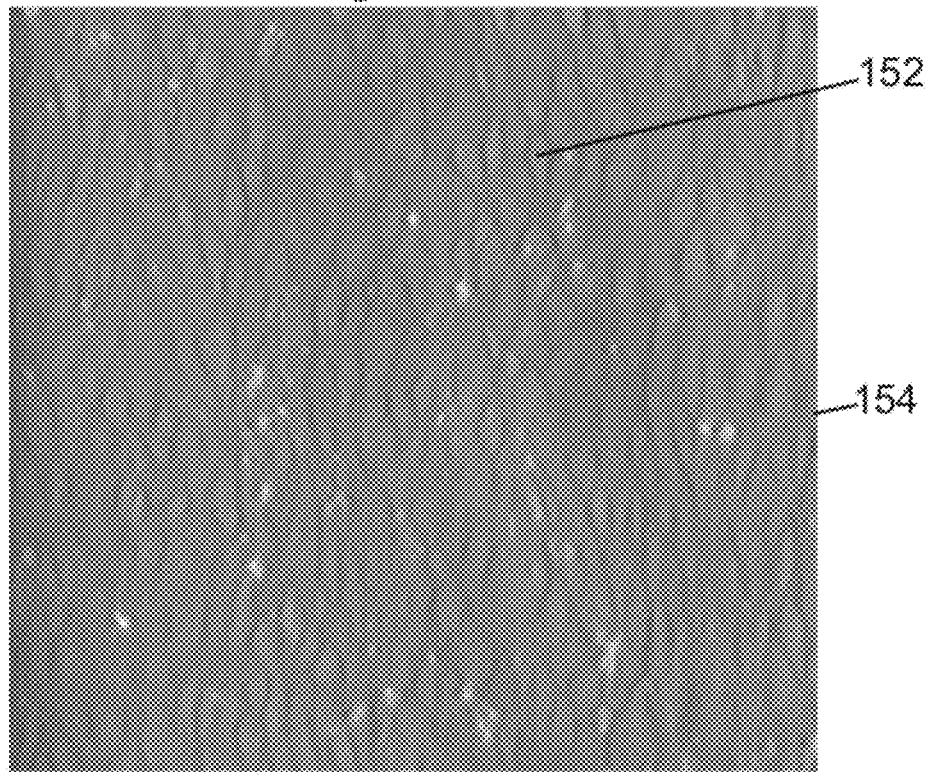
FIG. 1D is a picture of a kidney cell culture grown on a substrate with topographical patterning, according to an illustrative embodiment of the invention.

FIG. 1D is a picture illustrating the results of one possible embodiment of the invention. FIG. 1D shows a kidney cell culture grown on a substrate with a topological texture 154. As in the illustration, FIG. 1B, the cells 152 appear to grow in a more aligned and tightly connected manner.

Figure 2A:
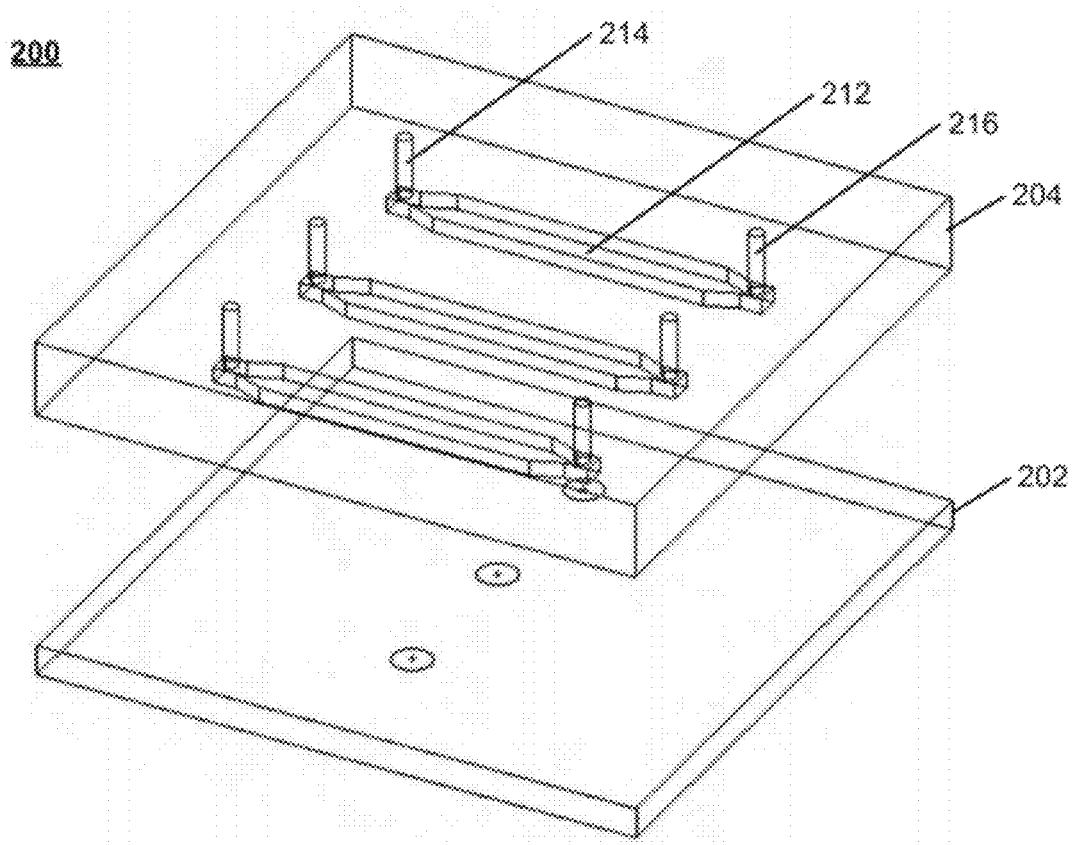
FIG. 2A is an exploded solid model of an apparatus with biomimetic flow channels, according to an illustrative embodiment of the invention.
Figure 2B:
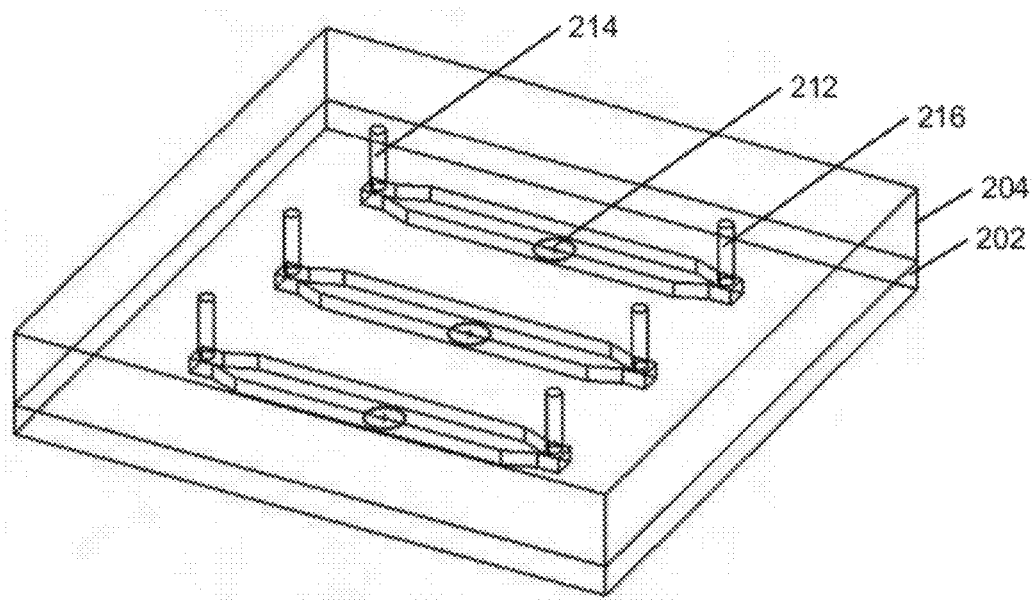
FIG. 2B is a solid model of the assembled apparatus with biomimetic flow channels from FIG. 2A, according to an illustrative embodiment of the invention.

FIG. 2A is an exploded solid model showing an exemplary embodiment of a device 200 for culturing cells in a biomimetic environment. FIG. 2B shows the assembled device. The device 200 includes a substrate 202 and a flow cell 204 having three flow channels 212. The top of the substrate 202 have a topographical pattern not shown in FIG. 2, such as the pattern of FIG. 1B. The walls of the flow channels 212 may also or alternatively have a topography, such as the pattern of FIG. 1B. Atop the surfaced side of the substrate 202 is a cell layer, with cells preferably confined to the area of the substrate underneath the flow channels 212 in the flow cell 202. The substrate 202 can be made of a thermoplastic, such as polystyrene or polyimide, biodegradable polyesters, such as polycaprolactone (PCL), or soft elastomers such as polyglycerol sebacate (PGS). The substrate 202 may alternatively be made of polydimethylsiloxane (PDMS), poly(N-isopropylacrylamide), or nanotubes or nanowires formed from, for example, carbon or zinc oxide. The substrate 202 can be made of any material upon which a micron-scale topography can be formed and upon which cells can be grown. Examples of topographical patterns are shown in FIGS. 7A-7D and FIGS. 8A-8F, and a method for chemically-patterning the substrate 202 is described in relation to FIG. 4. A method for growing the cell layer is described in relation to FIG. 5.

Figure 2C:
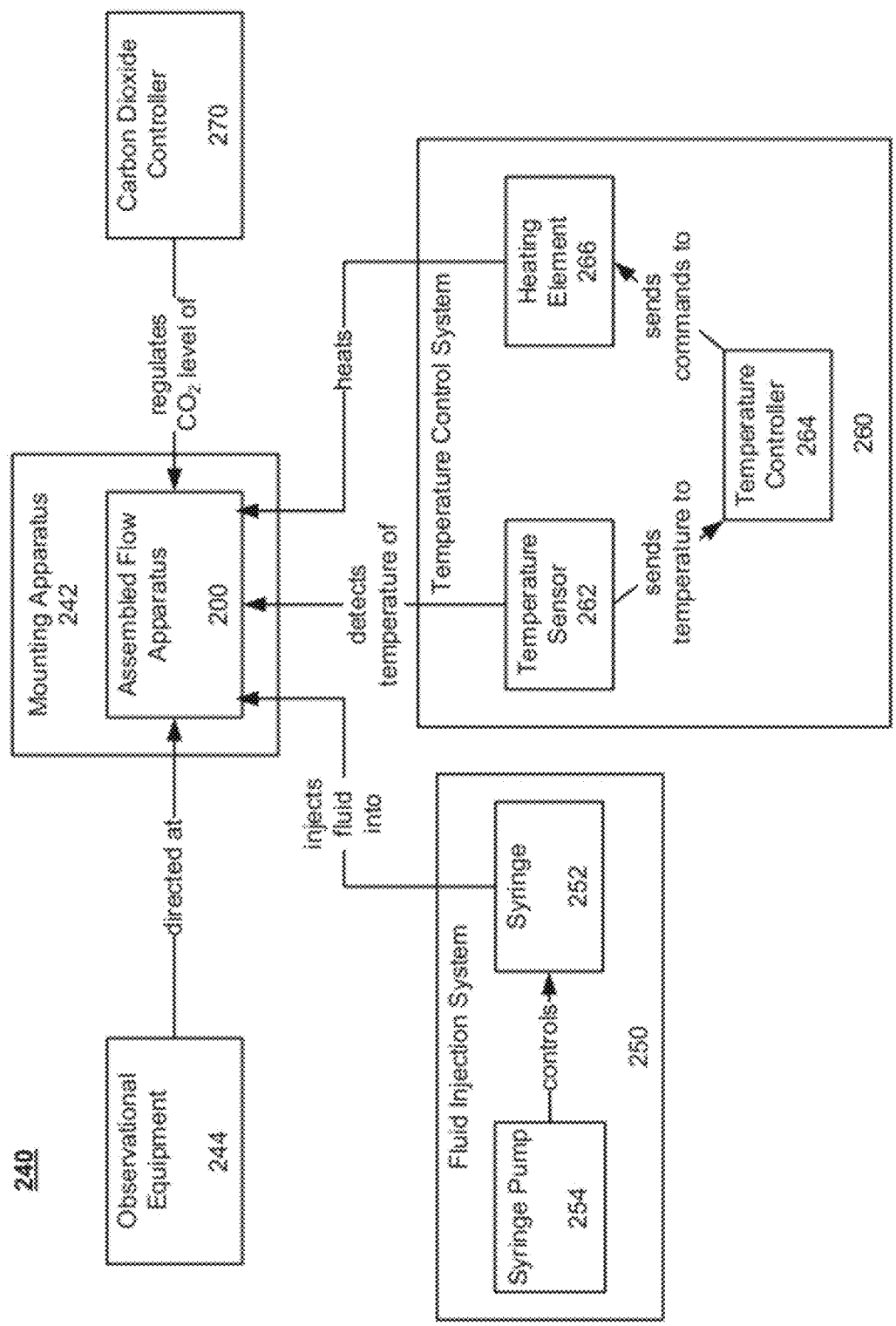
FIG. 2C is a block diagram of a flow system for use with the biomimetic flow apparatus of FIG. 2B, according to an illustrative embodiment of the invention.

The flow cell 204 has three flow channels 212 cut into the flow cell 204 from the bottom. In some embodiments, the flow cell is made of a translucent material such as PDMS. Alternatively, the flow cell may be made of other materials, such as any of the possible substrate materials listed above. A 3D solid object printer or photolithography may be used to create the flow channels 212 in the flow cell 204. As shown in FIG. 2B, when assembled, the substrate 202 forms the bottom wall of the flow channel, and the flow channel 212 in the flow cell contains the top wall and two side walls. The top, bottom, and side walls are collectively referred to as "walls" herein. The flow cell 204 and substrate 202 may be reversibly attached, so that after an experiment has been run, the flow cell 204 can be removed so that the cell layer can be examined. An inlet 214 and an outlet 216 allow tubing access to the flow channel 212. The inlet 214 provides access for introducing a fluid into the flow channel 212, and the outlet 216 provides access for removing fluid that has passed through the flow channel 212. The tubing that enters the inlet 214 connects to a means of controlling injection volume and speed into the flow channel 212, such as a syringe with a syringe pump. The fluid injection system may be part of a biomimetic flow system that the apparatus 200 is mounted in. A block diagram of an exemplary flow system 240 is shown in FIG. 2C. The flow system may contain additional features, such as temperature control system and observational equipment. The fluid flow introduced through the inlet port 214 creates a uniform laminar flow along the walls of the flow channel 212 and over the cultured cells along the bottom of the channel.

The laminar flow across the cultured cells mimics the flow of fluid within a nephron and introduces a shear stress between the fluid and the cultured cells. Adjusting the flow rate of the fluid causes the shear stress along the cells to change. In a renal proximal tubule, cells experience shear stress (fluid shear stress or "FSS") of around 1 dyne/cm$^2$; however, the shear stress experienced varies along the length of a nephron. Shear stress has been observed as low as 0.015 dyne/cm$^2$, so being able to vary the shear stress by controlling the flow rate allows a range of biomimetic conditions to be produced with a single device design. For a rectangular channel with a width w and height h, and a fluid with a viscosity m, the wall shear stress t and flow rate Q have the following relationship:

$$\tau = \frac{6\mu Q}{bh^2}$$

In addition to varying the shear stress of a channel by changing the flow rate, the shear stress in a single channel can vary along the length of the channel if the geometry of the channel changes along the length of the channel. For example, in a flow channel having a first height in a first region of the channel along the direction of the flow and a second, lower height in a second region of the channel, the fluid flowing in the shorter second region of the channel has a higher flow rate than in the taller first region. Thus, the cells in the second region experience a higher shear stress than the first region. By smoothly varying the channel height, the cell layer experiences a gradient in shear stress. The varying shear stresses can be used for replicating different parts of a nephron, which may have different functions. Additionally, different types and arrangements of cells are associated with regions of the nephron that experience different levels of shear stresses, so regions along the substrate having different types or arrangements of cells can be lined up with a flow channel of varying height so that cells experience the appropriate shear stress.

The flow channels 212 in FIG. 2 have rectangular cross sections, but flow channels may have non-rectangular cross sections for different fluid dynamics. For example, the flow channel may have a semicircular, triangular, or trapezoidal cross section. The shear stress can be determined using the shear stress equation for the cross-section geometry. The flow channel may have two or more different cross section shapes along its length.

The assembled flow apparatus 200 may be placed in a flow system 240, shown in the block diagram of FIG. 2C, for holding the assembly and controlling the flow channel environment. The flow system includes a mounting apparatus 242, observational equipment 244, a fluid injection system 250, and a temperature control system 260.

The mounting apparatus 242 includes a plastic cover and plastic base made using, for example, a 3D solid object printer. The flow channel apparatus 200 is positioned between the cover and base of the mounting apparatus 242 which are held together by, for example, screws or clamps. Thus, the mounting apparatus 242 holds the substrate 202 and flow cell 204 of the apparatus 200 together, preferably forming a reversible seal so that no fluid can leak out of the flow channel 212.

The observational equipment 244 is used to observe the cells during and/or after the experiment while the flow channel apparatus 200 is held in the mounting apparatus 242. If a wall of the channel is transparent, an optical microscope can be used to observe the sample during the experiment. In some embodiments, the observational equipment includes a light source directed into the flow channel and optical sensors underneath the flow channel for detecting extraordinary optical transmission ("EOT") signals. In such an embodiment, both the flow cell 204 and substrate 202 should be made of a material that allows optical transmission. In other embodiments, electrodes are placed in the flow channel for detecting confluence, shape, and metabolism of the cells. In some embodiments, imaging is performed outside of the mounting apparatus, possibly after the flow channel apparatus 200 has been disassembled, and the flow system 240 does not have observational equipment 244.

The fluid injection system 250 includes a syringe 252 and a syringe pump 254. The syringe 252 contains the fluid to be flowed through the flow channel 212, and the syringe pump 254 controls the syringe 252 to control the amount of fluid flowed, the flow rate, and the length of time that fluid is flowed. The fluid injection system 250 can be used to inject two or more different fluids, including, but not limited to, a buffer fluid, a reactant fluid, a fixing solution, and a stain. The fluid injection system 250 may also include means to combine the fluids; for example, the syringe pump 254 may include a valve for introducing a reactant into the buffer solution, or for introducing a stain into the buffer solution. The syringe pump 254 may be controlled by a processor, such as a general purpose processor.

The substrate 202 and/or flow cell 204 may be made of an insulating material to maintain a temperature stability within the flow channels 212. The flow system 240 can include a temperature control system 260 or incubator. The temperature control system includes a temperature sensor 262, a temperature controller 264, and a heating element 266 to maintain the flow channels 212 at a biomimetic temperature, i.e., 98.6° F. The temperature can be selected to be higher or lower to simulate different conditions, e.g., fever or injury. The temperature 262 sensor detects the system temperature and sends it to the temperature controller 264. Based on the current system temperature, the temperature controller 264 determines if heat should be added to the system. The temperature controller 264 sends commands to the heating element 266, such as a thermistor, to add heat to the system as necessary. In some embodiments, the temperature system can also cool the apparatus 200. The temperature controller or a second temperature controller also maintains the temperature of the fluids to be flowed into the flow channels 212. The flow system 240 also can include a carbon dioxide controller 270 to regulate the carbon dioxide level inside the flow channel. The carbon dioxide controller 270 can include a carbon dioxide sensor, a processor, and means for increasing or decreasing carbon dioxide levels as necessary. In some embodiments, the carbon dioxide controller is integrated into the temperature control system 260.

In some embodiments, the flow system 240 is connected to a computer with a general purpose processor. The computer can act as temperature controller 264, and temperatures from the temperature sensor 262 are sent to the computer and saved to memory. Similarly, the computer can act as a carbon dioxide controller, and carbon dioxide levels from a carbon dioxide sensor can be sent to the computer and saved to memory. The computer can also control the syringe pump 254 to automate the fluid flow and save data about the fluid flow. The computer can also control the observational equipment, save images or other data obtained from the observational equipment, and perform analysis on the data.

The apparatus 200 may contain more or fewer flow channels 212 than three. A high-throughput apparatus may be produced containing a hundred or more flow channels 212. In some embodiments, the high throughout apparatus contains ninety-six flow channels. The inlets 214 of two or more flow channels 212 may be fluidly connected so that fluid is flowed through multiple flow channels 212 simultaneously and, if the geometries of the flow channels 212 are identical, at the same flow rate. The flow system 240 may be configured to automatically run multiple experiments at the same time or perform experiments one at a time. An experiment performed in one flow channel in the apparatus 200 could differ from an experiment performed in a different flow channel in at least one of a fluid, a flow rate, the flow channel geometry, and the temperature. The apparatus 200 may be disposable or, after use, all or a portion of the apparatus (e.g., the substrate 202 or the flow cell 204) may be disassembled and cleaned for reuse.

Figure 3:
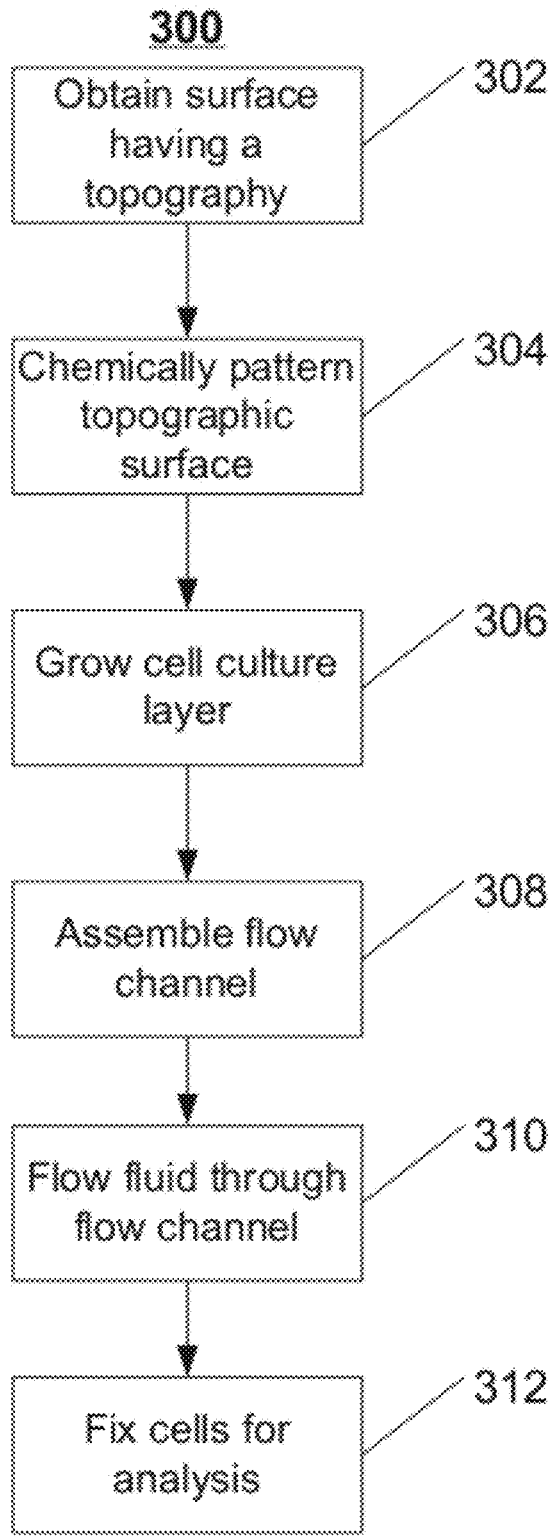
FIG. 3 is a flowchart for a method for creating and using one of the biomimetic flow channels of FIG. 2, according to an illustrative embodiment of the invention.

FIG. 3 is a flowchart for a method 300 of creating and using one of the biomimetic flow channels shown in FIG. 1. The method 300 includes the steps of obtaining a surfaced substrate (302), chemically patterning the substrate (304), growing a cell layer (306), assembling the flow channel (308), flowing fluid through the flow channel (310), and fixing the cells for analysis (312).

The first step 302 is to produce or obtain a surface with a topographical pattern such as the grooves 156 and ridges 158 on the surface 152 of FIG. 1B. The surface may be created using, for example, direct lithography, photopatternable resists, injection molding, direct micromachining, deep RIE etching or hot embossing or any combination thereof. An exemplary method for producing a surfaced substrate by hot embossing for use in the apparatus 200 is described in relation to FIG. 4. In some embodiments, a thin layer of metal, such as gold, is evaporated onto the topographical surface to aid in optical imaging for analyzing the sample. In some embodiments, the metal layer allows analysis of the cell culture using optical sensors for detecting surface plasmon resonance (SPR). In some embodiments, the metal layer is also useful to chemically pattern certain cytophilic and cytophobic molecules on the substrate due to the strong affinity of the molecular head group to the metal. The metal layer is thin enough so that the topography of the surface is maintained. The metal layer may have nanoholes for use in SPR detection. The nanoholes may be on the order of 100 nm wide and milled into the metal using, for example, photolithographic techniques, electron beam lithographic techniques, a focused ion beam (FIB), or other methods. The metal layer could alternatively be made of silver, aluminum, beryllium, rhenium, osmium, potassium, rubidium, cesium, rhenium oxide, tungsten oxide, copper, titanium, or another material suitable for imaging or other analysis. In some embodiments, a thin layer of chromium or other metallic bonding agent is first evaporated onto the surface before the layer of gold or other metal.

Next, the textured surface is chemically patterned (step 304) to produce cytophobic and/or cytophilic regions for isolating cell growth to the flow channel areas. If kidney cells are grown across an entire surface, such as substrate 202, then sealing the flow cell 204 to the substrate 202 would crush the cells in the regions outside of the flow channel 212. This creates leakage of contents from the crushed cells into the flow channel 212, which can provide biochemical signals received by the surviving cells. Such leakage could have undesirable effects on the experimental procedure. Thus, cells should be restricted to the regions of the surface that form the walls (i.e., top, bottom, and/or sides) of the assembled flow cell. For the apparatus 200, the cell layer is restricted to the regions of the substrate 202 that do not contact the flow cell 204, i.e., the regions below the flow channels 212. To create these regions, cytophilic materials can be placed on the flow channel surfaces to promote cell growth for regions within the flow channel. Additionally or alternatively, cytophobic materials can be placed on surfaces which do not form a wall of a flow channel to prevent cell growth outside of the flow channel surface. Once the topographical surface has been created and chemically patterned, an ECM protein is applied to the surface and a cellular suspension is placed above the protein layer to grow a cell culture (step 306), which contains one or multiple types of cells. One method for creating cytophilic and cytophobic regions of a surface, such as substrate 202, and growing cells on the surface is described in relation to FIG. 5.

Once the cells are grown (step 306), the flow channel is assembled (step 308). In some embodiments, the flow cell is reversibly assembled so that at least one wall can be removed for observation. In some embodiments, the flow cell 204 is placed on top of the substrate 200 and attached using, for example, screws or clamps. Alternatively, the apparatus 200 may be assembled within the mounting assembly 242 as described in relation to FIG. 2C. A fluid is then flowed through the assembled flow channel (step 310). The flow rate is selected to create the desired shear stress as described in relation to FIG. 2, and the flow rate is controlled by the fluid injection system. The fluid may contain a reagent and a buffer fluid. The reagent is chosen based on the experiment being performed; for example, the fluid may include a pharmaceutical agent or a potential toxin to test the efficacy or toxicity of the substance. The fluid may be flowed through the flow channel for any duration, for example, on the order of seconds, minutes, hours, or days. The duration of fluid flow depends on the type of experiment being performed. For example, an experiment for imaging the cells experiencing a particular shear stress may only last a short duration, on the order of tens of seconds to several minutes. On the other hand, an experiment for determining the effect of a potential toxin or a potential therapeutic agent on the cells may require a longer exposure time, on the order of several hours, several days, or longer. The flow rate may vary over time, and in some embodiments, the cells may experience intermittent fluid flow.

Next, if post-flow analysis is to be performed, the cells are fixed for analysis (step 312). First, the cells may be rinsed by flowing a second solution, such as phosphate buffered saline (PBS), through the flow channel. Then, a third solution containing a fixative, such as formaldehyde or other aldehyde, is flowed through the channel so that the channel can be disassembled without damaging the cells. The percentage of fixative in the solution and the type of fixative chosen depends on the method of analysis and the type of cell in the flow channel. The rinsing solution and fixative are injected through the inlet 214 using the fluid injection system. The same injection mechanism, such as the syringe pump, and tubing may be used and the syringe swapped out, or the mounting apparatus may contain at least two or three syringe pumps connecting via tubing to the same inlet. A stain may also be applied to the cells before or after disassembling the flow channel to increase contrast for imaging.

FIG. 4 is a series of diagrams illustrating a method for producing a surface with topographical patterning such as surface 102 from FIG. 1. The method involves etching a silicon oxide master mold (steps A-E), electroforming a negative nickel mold (step F), and using hot embossing to produce the topographical surface from the nickel mold (steps G-I). The silicon oxide master mold is created using photolithography techniques. Step A illustrates coating a photoresist solution 404 onto a silicon oxide wafer 402. The photoresist 404 can be applied using spin coating. After spin coating, the silicon oxide wafer 402 may be baked to evaporate residual solvent. A photo mask 406 is then layered on top of the photoresist 404 (step B) to photolithographically pattern the resist 404. In FIG. 4, the photo mask 406 has the cross-section of a ridge pattern. The pattern of the topography is determined by the photo mask selected. Alternative topographical patterns, which would be made with different photo masks, are shown in FIG. 6. The photoresist 404 is developed to create an etch mask 410 (step C) by exposing the top surface to light 408. In FIG. 4, a negative photoresist 404 is used, so the portion of the photoresist layer 404 that is exposed to light 408 becomes insoluble in the developer, while the unexposed portion is soluble and is dissolved when developed. Alternatively, a positive photoresist can be used. Once the pattern has been generated in the photoresist 404 to produce the etch mask 410, the silicon wafer may again be baked, and the wafer 402 is developed to remove the photoresist 410 from the areas exposed to the light. Finally, the silicon oxide wafer 402 is etched using a chemical agent that removes the uppermost layer of the wafer not protected by etch mask 410 (step D). In some applications, the depth of silicon oxide removed is on the order of 1 micron. To produce a pattern with square edges as seen in FIG. 4, an anisotropic etchant is used; if rounded wells are desired, an isotropic etchant can be used. Finally, the etch mask 410 is stripped to create the master mold 412 (step E).

Other methods can be used to create the master mold 412. For example, electron beam lithography or other nanolithography techniques can be used to etch features into the resist, particularly if the desired topography includes very small-scale features with widths on the order of nanometers or tens of nanometers.

Once the master mold 412 has been created, nickel 414 is electroformed to the silicon wafer (step F). A nickel source 414 and the master mold 412 are placed in an electrolytic bath. A power source 416 creates a voltage difference between the nickel source 414 and the silicon oxide master mold 412 that causes nickel to electroplate onto the master mold 412 to form a nickel mold 418 that is a negative of the master mold 412. The nickel mold 418 is separated from the master mold and placed face down and pressed against a thermoplastic 420. The thermoplastic is pushed into the grooves in nickel mold 418 through hot embossing (step G). Elevated heat and pressure causes the thermoplastic 420 to fill into the nickel mold. Then, the embossed thermoplastic 422 is cooled under constant pressure (step H) before being removed from the nickel mold 418 (step I). The topographical surface in the molded thermoplastic 422 can then be used as a wall of a flow channel.

Figure 5:
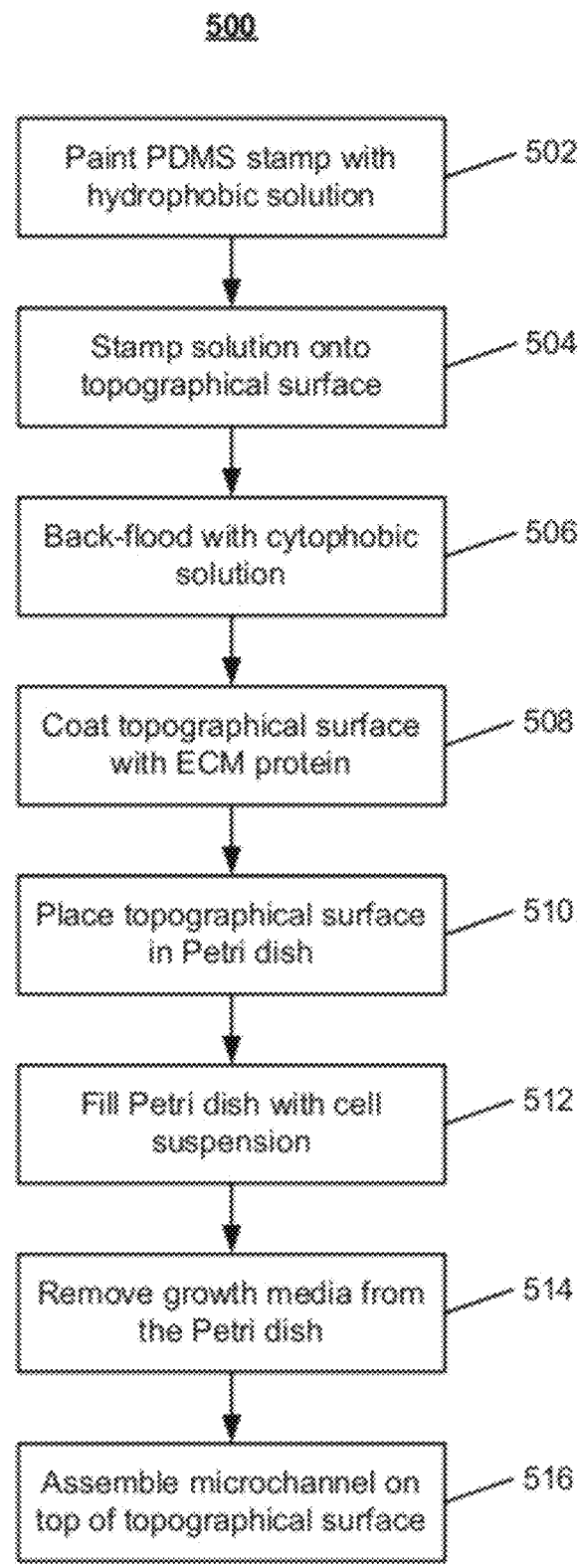
FIG. 5 is a flowchart for a method for creating cytophilic and cytophobic regions on a surface and growing cells on the surface, according to an illustrative embodiment of the invention.

FIG. 5 is a flowchart for a method 500 of creating cytophilic and cytophobic regions of a surface and growing cells on the surface, according to an illustrative embodiment of the invention. The method involves creating a hydrophobic region on a surface for the area that will form a wall of a flow channel (steps 502 and 504), filling in the rest of the surface with a hydrophilic substance (step 506), coating the hydrophobic region with a protein (step 508), and growing a cell layer atop the protein, i.e., the cytophilic region (steps 510 and 512). In general, extracellular matrix (ECM) proteins adhere to hydrophobic molecules. Cells thrive in conditions similar to in vivo conditions, so cells tend to grow in regions containing ECM proteins rather than hydrophilic regions that do not contain ECM proteins.

First, a hydrophobic solution is applied to a PDMS stamp (step 502) and stamped onto a surface having a topography (step 504). The stamp is held with pressure and released so that a hydrophobic self-assembled monolayer (SAM) of molecules remains on the surface. Molecules used for a hydrophobic SAM typically have a head group that binds to the substrate and a hydrophobic tail group, such as CH3, that binds to ECM proteins. In some embodiments, hexadecanethiol is used for the SAM. Other molecules that can be used for the SAM include alkyl thiols, functionalized thiols, dithiols, and silanes.

The painted surface of the PDMS stamp can be the size of the side of the flow channel being stamped, or the painted surface could only cover the area of the flow channel to be filled with cells. For example, if it is not desired to have cell growth near the ends of the channel by the fluid inlet and outlet, a rectangular stamp to cover only the central part of the flow channel would be used. For an apparatus with multiple flow cells, a single PDMS stamp may have a pattern for stamping the walls of multiple flow channels.

The rest of the surface is back-flooded with a hydrophilic solution, such as polyethylene glycol (PEG), to form a SAM that discourages cell growth on the parts of the surface which will not be flow channel walls (step 506). As described in FIG. 1, this keeps cells from growing outside of the desired area to prevent leakage from cells crushed when the apparatus is assembled as well as unwanted edge effects, such as negative communication between crushed cells and cells within the channel.

The topographical surface with the two SAMs is coated with an extracellular matrix (ECM) protein (step 508). The protein adheres to the hydrophobic SAM, but the hydrophilic SAM suppresses protein adsorption. This causes the protein to concentrate in the hydrophilic region that will form a wall of the flow channel when the apparatus is assembled. In some embodiments, different types of cells may be grown in different regions of a flow channel or on different flow channels having walls formed on the same surface. To isolate cell types to certain regions of the surface, the surface may be treated with different proteins and/or SAM molecules to promote growth of certain cell types in certain regions. Other methods can be used to create a cytophilic region. For example, a thermopolymer substrate can be treated with an oxygen plasma to increase cytophilicity, and any untreated region will be cytophobic.

The treated surface is then placed in a Petri dish to grow the cells (step 510). The Petri dish is filled with a cell suspension solution and placed in an incubator set at 5% $CO_2$ and 37° C. in some embodiments (step 512). Cells adhere only to the protein-coated cytophilic region. The cells are cultured to a high confluency so that the when assembled, the flow channel wall will be covered in a layer of cells. Cells that are commonly grown for in vitro kidney models include human proximal tubule cells, such as cells from the HK-2 line; renal proximal tubule epithelial cells (RPTEC); Madin-Darby canine kidney (MDCK) cells; and primary inner medullary collecting duct (IMCD) cells or primary proximal tubule cells, commonly collected from mice or rats. In various embodiments, stem-cell derived cells, kidney progenitor cells, or cells harvested from kidney tissue are grown. Additionally or alternatively, in some embodiments, cells used in the present technology include stem-cells (e.g., embryonic, adult, induced pluripotent) and/or endothelial cells. Cells from humans, other mammalian organisms, or other organisms may be grown.

Once the cells are grown, the media in which the cells were grown in was removed (step 514). Typically, the media is removed from the areas outside of the cell layer. Thus, some moisture remains within the region with the cell layer, but the rest of the substrate is dry. Then, the flow microchannel is assembled atop the topographical surface (step 516). Once the flow microchannel is on top of the topographical surface, the microchannel can be filled with the cell growth media.

Figure 6A:
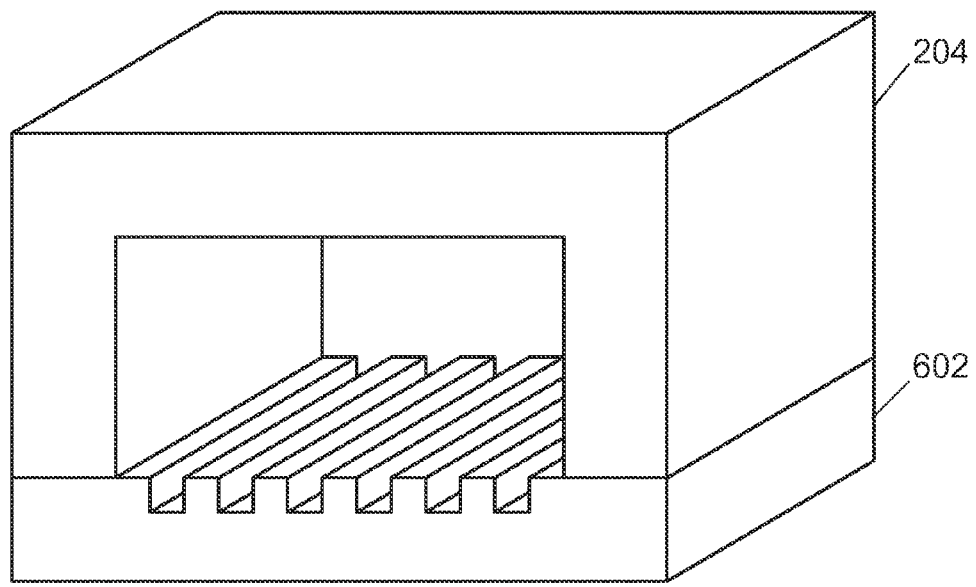
FIGS. 6A, 6B, 6C and 6D are perspective views of cross sections of three illustrative embodiments of biomimetic flow channels with different topographical characteristics.

FIG. 6A shows a perspective view of a cross section of an illustrative embodiment of a biomimetic flow channel with ridges and grooves parallel to the direction of the flow channel. The ridges and grooves may not be to scale. As described in relation to FIG. 1, the width of the ridges and grooves may be in the range of 20 nm to 5 microns. For example, the width of the ridges and/or grooves may, independently, be 20-40 nm, 30-50 nm, 50-100 nm, 100-200 nm, 200-400 nm, 400-600 nm, 600-800 nm, 800 nm-1 micron. By way of further example, the width of the ridges and/or grooves may be, independently, 1-2 microns, 2-3 microns, 3-4 microns, or 4-5 microns. The height of the flow channel may be in the range of 100 to 200 microns. Larger or smaller heights can be used, but if a flow channel is much narrower than 100 microns high, fluid flowing through the channel may not be in laminar flow. In the embodiment shown in FIG. 6A, the cell layer would be grown above the bottom layer 602 of the flow channel, and the ridges and grooves would cause the cells to align parallel to the direction of flow through the channel.

Figure 6B:
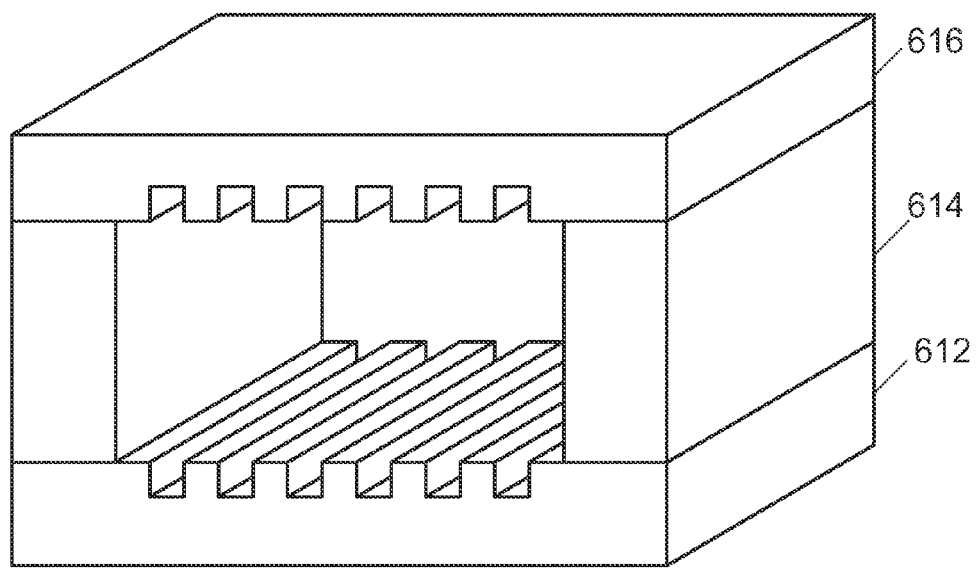

In the embodiment shown in FIG. 6B, both the bottom surface and the top surface are textured and cells are cultured on both, which may better replicate an in vivo nephron or another organ. The bottom layer 602 in FIG. 6A and the top and bottom layers 612 and 616 in FIG. 6B and layers 632, 636, and 640 in FIG. 6D may be topographical substrates such as substrate 202 of FIG. 2. In some embodiments, layer 616 in FIG. 6B has at least two holes through it so that fluid can be flowed into the flow channel through one hole and removed through the other. In FIG. 6B, a middle layer 614 having an elongate hole formed therethrough is sandwiched between the top and bottom layers 616 and 612. When positioned between the top layer 616 and bottom layer 612, the side walls of the elongate hole form the side walls of a flow channel.

Figure 6C:
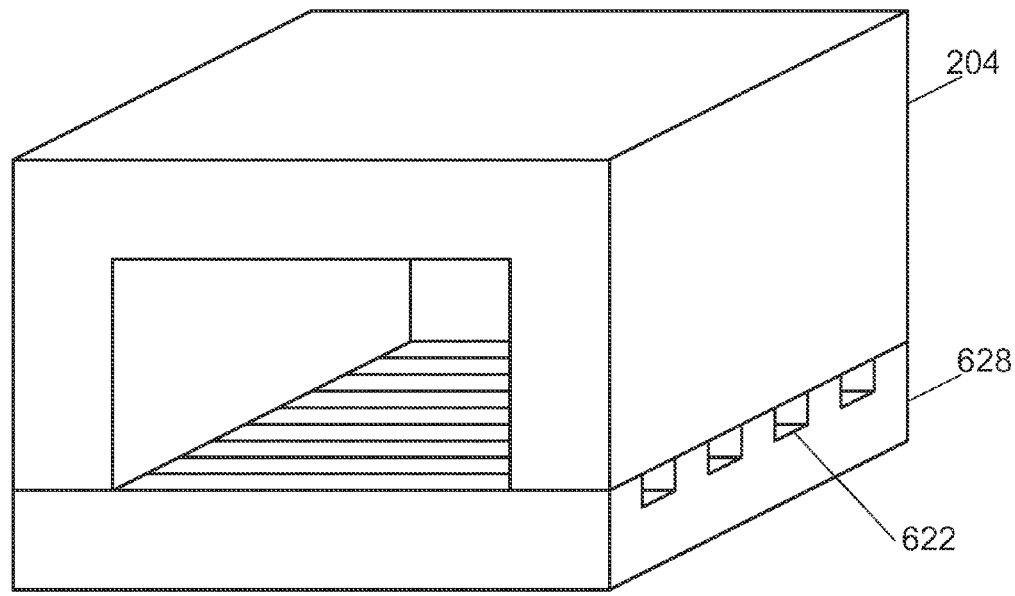

FIG. 6C shows a perspective view of a cross section of another illustrative embodiment of a biomimetic flow channel which has ridges and grooves perpendicular to the direction of the flow channel. The ridges and grooves may not be to scale. The dimensional ranges for the topography and flow channel of FIG. 6C are the same as the ranges given in relation to FIG. 6A. The cell layer would be grown above the bottom layer 622 of this flow channel, and the ridges and grooves would cause the cells to align perpendicular to the direction of flow through the channel. The top surface and/or side surfaces of the channel may also be textured and have cells grown thereon (not shown).

As can be seen at the right side of FIG. 6C, the entire top surface of the lower layer 622 is textured with ridges and grooves. Since the sides of the flow channel may not be sealed, fluid flowing through the flow channel may seep out of the sides of the flow channel through the holes 628 created by the grooves. So, in some embodiments, the topographical surface is created only on the part of the surface that will form a wall of a flow channel; the rest of the surface is smooth. This can be accomplished by using a photo mask that completely covers the surface of the substrate except for the regions that will be flow channel walls. When the flow channel is assembled, the smooth surface joined to the flow cell or side walls would create a seal at the sides of the flow channel along its length, preventing fluid from travelling sideways out of the ridges and grooves.

Figure 6D:
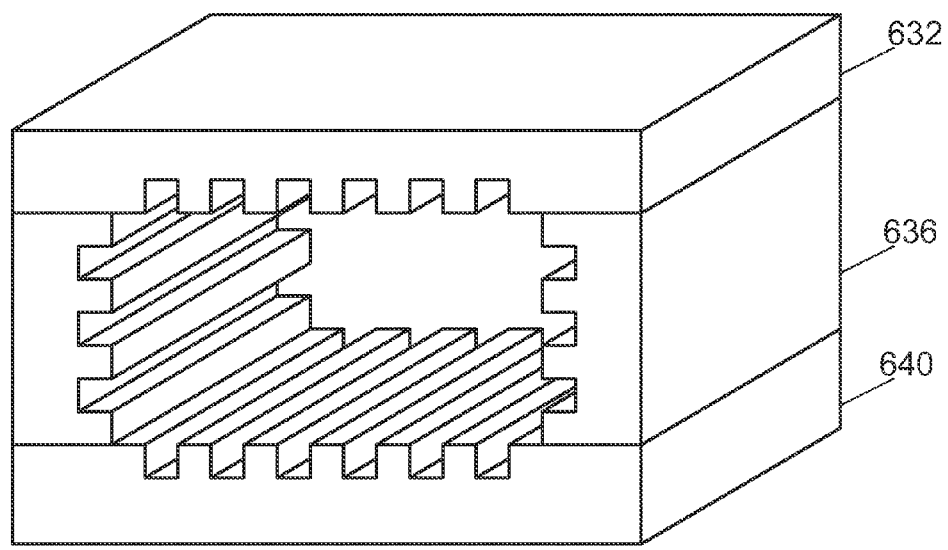

FIG. 6D illustrates a perspective view of another illustrative embodiment of a biomimetic flow channel. In this embodiment, the bottom, top and both side walls are textured and cells are cultured on each, which may better replicate an in vivo nephron or another organ. In this illustrative embodiment, the texture consists of ridges and grooves parallel to the direction of the flow channel. In some embodiments, layer 632 in FIG. 6D has at least two holes through it so that fluid can be flowed into the flow channel through one hole and removed through the other. An elongated hole is formed when the walls 636 are sandwiched between the top 632 and bottom 640 layers. The side walls of the elongated hole form the side walls of a flow channel.

FIG. 7 shows several embodiments of topographical patterns having variation in ridge and/or groove width. FIG. 7A is a perspective view of a substrate having a gradient in its topographical pattern. The widths of the ridges and grooves become narrow from left to right across the surface. A flow channel may be assembled atop the substrate to cause fluid to flow either parallel or perpendicular to the grooves. In some embodiments, the widths of the ridges stays constant while the widths of the groove changes; in other embodiments, the widths of the grooves stays constant while the widths of the ridges varies. A surface with variations in topography can be used in an experiment for examining the effect of different ridge and/or groove widths on a particular type of cell. Additionally, for an organ structure that has varying cell features across an area of the structure in vivo, smoothly varying surface topography as in FIG. 7A can be used to create a flow channel that mimics such a feature.

Figure 7A:
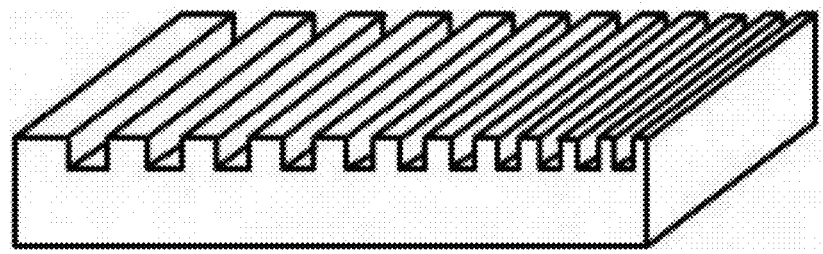
FIG. 7A is a perspective view of an illustrative embodiment of a substrate having a gradient in its topographical pattern.
Figure 7B:
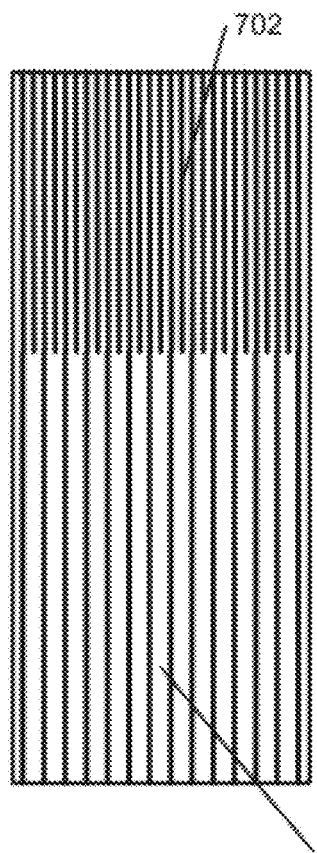
FIGS. 7B, 7C, and 7D are top views of three illustrative embodiments of flow channel surfaces having variations in their topographical patterns along the channel.
Figure 7C:
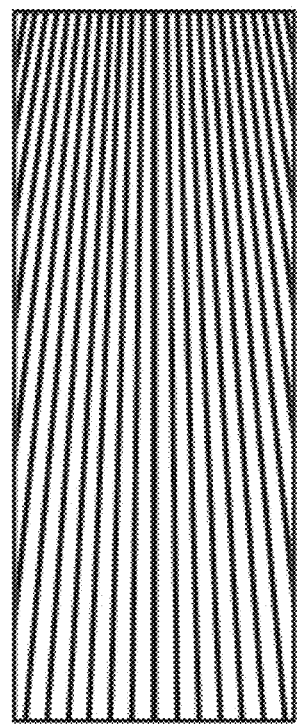
Figure 7D:
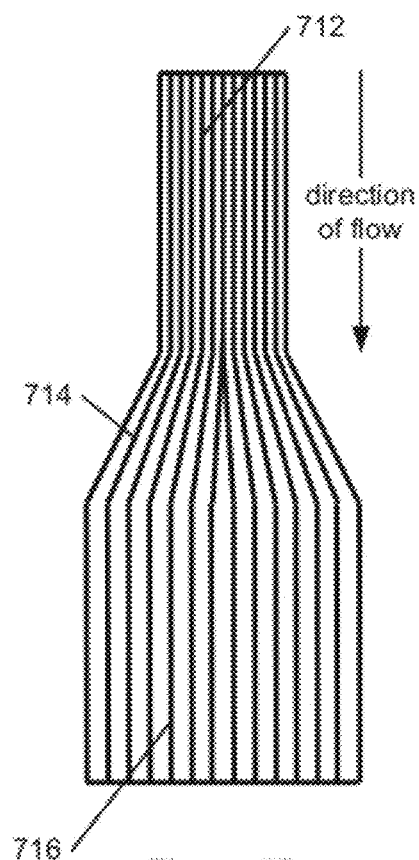

FIGS. 7B, 7C, and 7D are top views of flow channel surfaces having variations in their topographical patterns along the channel. The flow channels may not be to scale. The direction of flow across the channels is down the page, as shown by the arrow to the right of FIG. 7D. In other embodiments, fluid can be flowed in the opposite direction. FIG. 7B is a top view of a surface with two distinct regions 702 and 704 having different groove widths. The upper region 702 has a narrower groove width so that the grooves and the ridges are about the same width. The lower region 704 has noticeably wider grooves than the upper region 702. The grooves in the lower region 704 are also wider than the ridges. A flow channel having two distinct topographical regions can be used to mimic an in vivo structure that has two distinct cell types or cell arrangements. For example, a kidney tubule has cell types that change along its length, and variations in the basement membrane of a kidney tubule can be simulated in vitro by varying the topography of the flow channel.

The grooves of FIG. 7C also are wider towards the end of the flow channel; however, the ridges fan out so that the grooves widen smoothly, creating a smooth transition between the narrow grooves and the wider grooves along the channel rather than distinct regions. A flow channel with one or more sides of this type can be used to mimic an in vivo structure that has a gradient in cell type or cell arrangement across the structure. A flow channel with this type of topography could also be used in an experiment for examining the effect of different ridge and/or groove widths on a particular type of cell.

FIG. 7D is a top view of a non-rectangular channel having two regions of constant topography 712 and 716 that differ from each other and a transition region 714 between the two regions of constant topography. The start of the flow channel 712 has a narrow width and narrow grooves, and the end of the flow channel 716 is wider and has wider grooves. All of the regions 712, 714, and 716 have the same number of ridges. If the flow channel atop the surface of FIG. 7D has a constant height, the shear stress experienced in the first region 712 will be higher than the shear stress in the last region 716 since the channel width is smaller and the flow rate is higher in the first region 712 than in the last region 716. This effect can alternatively be achieved by varying the channel height. The transition region 714 helps maintain laminar flow as the geometry changes. The methods of manufacture described in FIGS. 3, 4, and 5 can be used to create flow channel devices with any of the topographies and geometries shown in FIG. 7.

Figure 8A:
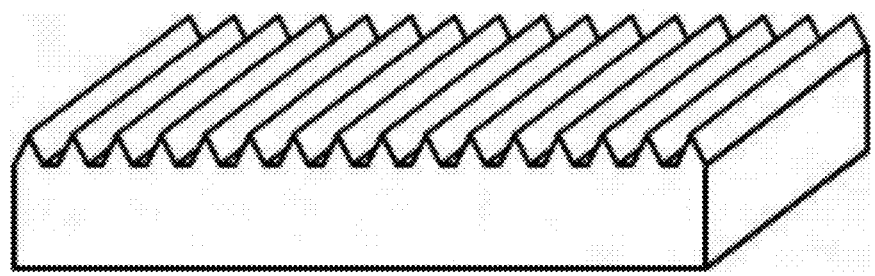
FIGS. 8A, 8B, 8C, 8D, 8E and 8F are perspective views of illustrative embodiments of three substrates having different topographical patterns.
Figure 8B:
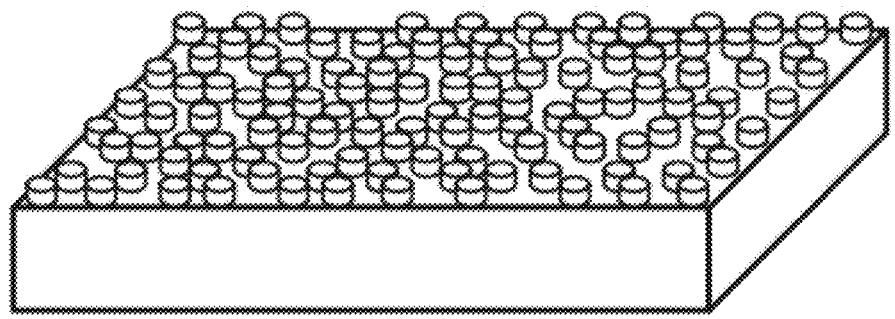
Figure 8C:
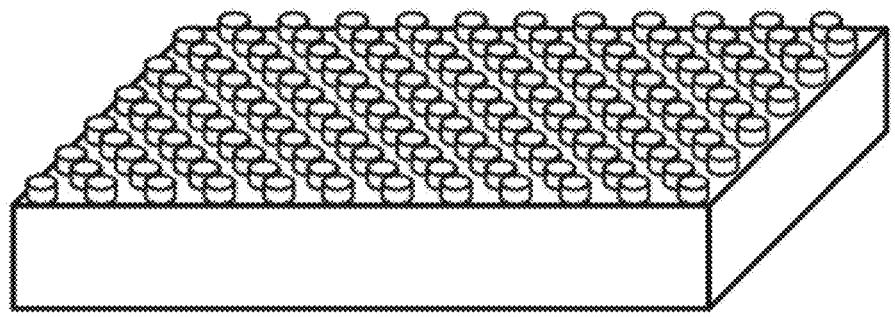
Figure 8D:
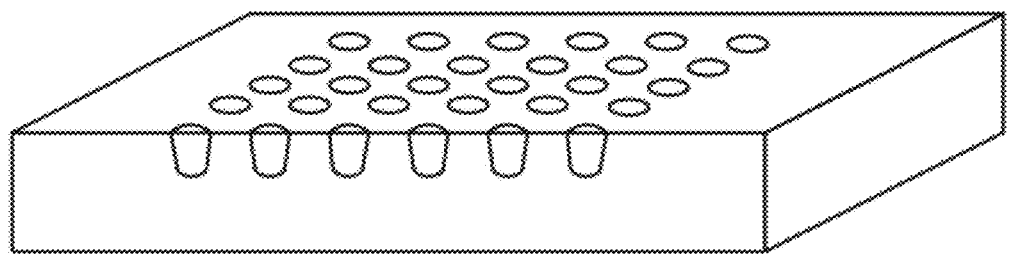
Figure 8E:
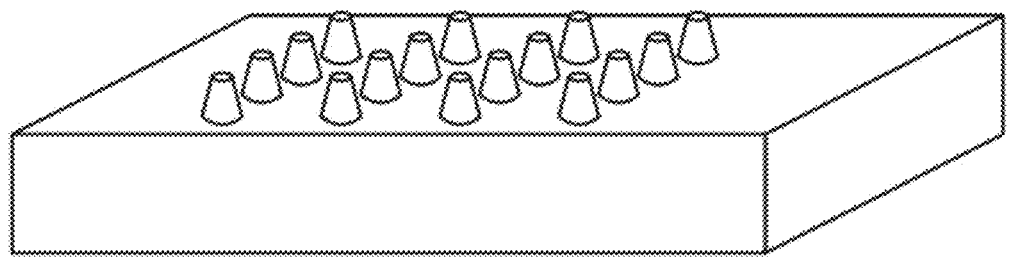
Figure 8F:
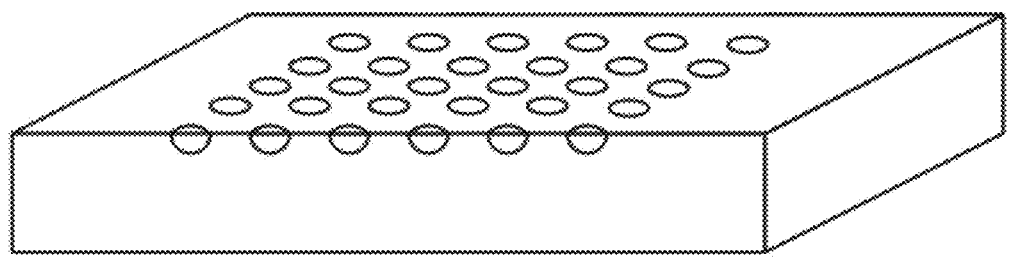

Surface topographies can have patterns other than the right-angled ridges and grooves shown in FIGS. 6 and 7. Some possible topographic surfaces are shown in FIGS. 8A through 8C, which are perspective views of three substrates with different topographical patterns. FIG. 8A shows triangular ridges separated by narrow grooves. The edges can be more rounded than are shown in FIG. 8A. FIG. 8B shows a random array of circular posts. FIG. 8C shows a linear array of posts. FIG. 8D shows a linear array of inverted cone pits. FIG. 8E shows a linear array of cone posts. FIG. 8F shows a linear array of inverted hemisphere pits. Any of the textures that can be broadly categorized as pits and posts can be arranged into random or linear arrays. Additionally, FIG. 8 is not intended to encompass all possible designs of pits and posts but rather provide an illustration of possible designs. The pit and post family may also include, but is not limited to, posts, cones, hemispheres, filleted pits, and chamfered posts. The topography selected depends on the type of cells being cultured, as different types of cells may have different in vivo environments and may respond differently to biomimetic cues. While ridges and grooves have been shown to provide biomimetic cues causing kidney cells to align, the extracellular matrix differs in different parts of the body, so cells in different organs or even other parts of the kidney may better mimic their in vivo characteristics when grown on the types of topographies shown in FIG. 8 or another type of topography. A method similar to the method described in relation to FIG. 4 can be used to form the substrates shown in FIG. 8A-8F. Other techniques may be used, particularly for producing triangular grooves or other patterns that have grooves with neither square nor rounded edges. As described in relation to FIG. 7, the size and/or separation of the features may vary along the surface, either in distinct regions or across a gradient. Additionally, a single flow channel may have multiple types of topographies, such as a region of posts and a region of ridges and grooves, or posts interspersed with ridges and grooves.

Figure 9B:
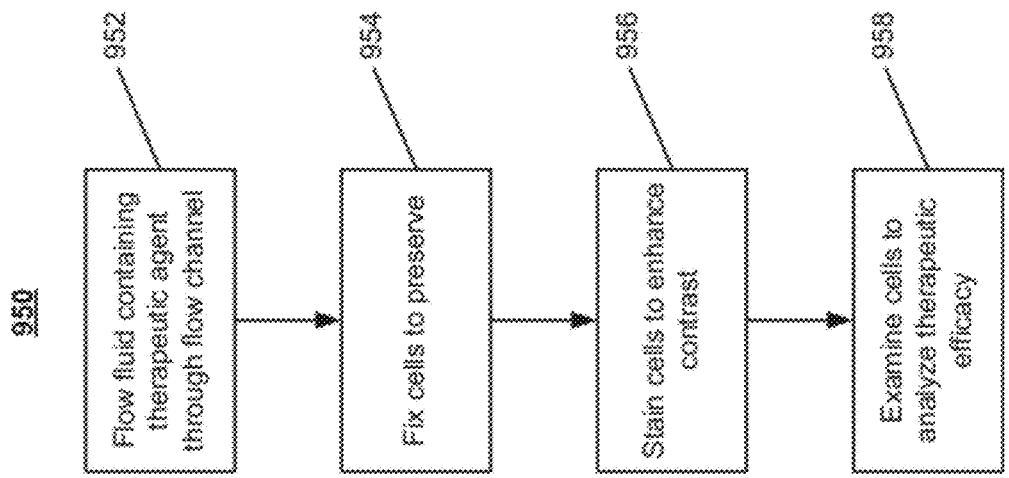
FIGS. 9A and 9B are flowcharts for methods for using one of the biomimetic flow channels of FIG. 2, according to an illustrative embodiment of the invention.
Figure 9A:
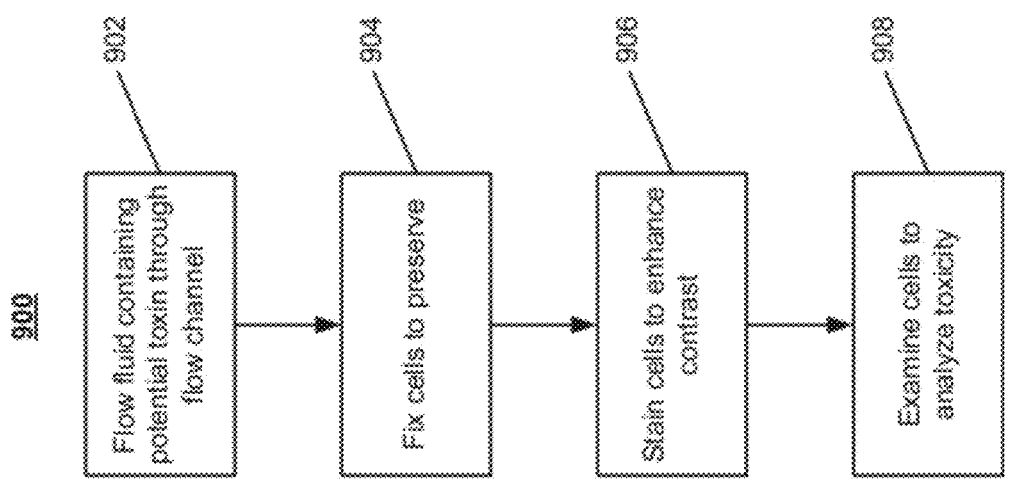

FIGS. 9A and 9B show two exemplary uses of biomimetic flow channels. FIG. 9A is a flowchart of a method 900 for using a biomimetic flow channel, such as the apparatus 200 of FIG. 2, to examine cell toxicity of a potential toxin. This method is useful in high-throughput drug screening; researchers can screen cytotoxic compounds before investing in further pharmaceutical development of the compound. For toxicity testing, a material that is potentially toxic to a type of cell is put in solution at a certain concentration and flowed through a flow channel containing a culture of the type of cells (step 902) according to the method described in relation to step 310 FIG. 3. In some embodiments, particularly if the potential toxin is difficult to manufacture or difficult to acquire, the injection system includes an injection valve that releases the potential toxin after a buffer fluid has established laminar flow within the flow channel. Using an injection valve minimizes the amount of potential toxin consumed in the experiment. If observational equipment is directed at the flow channel, the sample may be analyzed while the potential toxin is flowed through the channel.

After the potentially toxic solution has been flowed through the channel, the cells are rinsed and fixed (step 904) to preserve the results of the experiment for observation, according to the method described in relation to step 312 of FIG. 3. A stain or fluorescent tag is then applied to the cells before or after disassembling the flow channel to increase contrast for imaging (step 906). Any staining method, such as heaematoxylin and eosin (H&E) staining, silver staining, or immunofluorescent staining that is suitable for the cell type and observational equipment can be used. In some embodiments, the stain is a vital dye, such as trypan blue or propidium iodine, which cannot pass through the cell membranes of healthy cells. The vital dye is introduced into the flow channel with the potential toxin. If the compound is toxic, it may cause breakdown of the cell membranes and permit the dye to pass through the membranes and stain the cells.

Once the fluid has been flowed through the channel and the cells are prepared, the cells are analyzed to determine the toxicity of the potential toxin (step 908). In various embodiments, toxicity is determined using permeability assays, cell activity assays, metabolic activity assays, or live/dead assays. If the substance is toxic, it may have caused the cells to undergo necrosis, cause the cells to stop growing and dividing, or cause apoptosis. Cells undergoing necrosis may rapidly swell, lose membrane integrity, shut down metabolism, and release their contents. As described above, the use of a vital dye can show such effects. Vital dye staining and/or other effects of cell death can be viewed using, for example, an optical microscope, an electron microscope, or a digital holographic microscope. Other techniques for determining the viability of the cells during or after the experiment can be used. A cell counter, such as a CASY counter or a Coulter counter, can count the number of viable cells. If the surface under the cells includes gold electrodes, an ELECTRIC CELL-SUBSTRATE IMPEDENCE SENSING (ECIS) based approach can be used as a sensor of the confluence, shape, and metabolism of the cells.

FIG. 9B is a flowchart of a method 950 for using a biomimetic flow channel, such as the flow channel 212 of FIG. 2, to examine the efficacy of a potential therapeutic agent. The method 950 can be used in high throughput screening to determine if a potential pharmaceutical compound may have a therapeutic effect. For efficacy testing, a compound that is potentially beneficial to a type of cell in a flow channel is put in solution at a certain concentration and flowed through the flow channel (step 952) according to the method described in relation to step 310 FIG. 3. In some embodiments, particularly if the compound is difficult to manufacture or difficult to acquire, the injection system may include an injection valve that releases the compound after a buffer fluid has established laminar flow within the flow channel. If observational equipment is directed at the flow channel, the sample may be analyzed while the compound is flowed through the channel.

After the solution has been flowed through the channel, the cells are rinsed and fixed (step 954) to preserve the results of the experiment for observation, according to the method described in relation to step 312 of FIG. 3. In some embodiments, a stain or fluorescent tag can be applied to the cells before or after disassembling the flow channel to increase contrast for imaging (step 956). Any staining method, such as heaematoxylin and eosin (H&E) staining or silver staining, that is suitable for the cell type and observational equipment can be used.

Once the cells are prepared, they are analyzed to determine what effect, if any, the compound has had on the cells (step 958). Reagents that bind to particular proteins or nucleic acids can be applied to the cell layer to determine the presence of the protein or nucleic acid during analysis. Physical effects of the potential therapeutic compound can be viewed using, for example, an optical microscope, an electron microscope, or a digital holographic microscope. The features of interest depend on the type of cells and the desired effect of the pharmaceutical being researched. The method for analysis should be chosen according to which cellular features a research is interested in.

While preferable embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

In some embodiments, one or more topographical surfaces are formed in a bioartificial device for replicating or substantially replicating organ function by mimicking kidney or nephron functions, such as the device described in U.S. Pat. No. 7,790,028 entitled Systems, Methods, and Devices Relating to a Cellularized Nephron Unit, which was filed on Sep. 28, 2005 and issued on Sep. 7, 2010. Any of the features of an artificial kidney, including the Loop of Henle, distal tube, collecting duct, and associated blood vessels may include one or more of the topographical surfaces described above for better replicating in vivo conditions of a kidney. For example, the surfaces of the blood flow layer and/or the filtrate layer may have topographies formed therein. Cell layers including water-permeable cells, salt pumping cells, or other types of cells may be grown on a topographical surface or portions of a topographical surface. More particularly, the topographies for each channel are selected such that the cells grown thereon take on the morphology and phenotype of the desired portion of the kidney. Thus, in one embodiment, portions of the channels seeded with salt pumping cells are formed having a first nano-topography and portions of the channels seeded with water-permeable cells are formed with a different nano-topography. Any of the fabrication techniques or combination of fabrication techniques described herein or in U.S. Pat. No. 7,790,028 can be used for making such a bioartificial device.

Exemplary Bioartificial Apparatus

By way of example, but not by way of limitation, an illustrative embodiment of an integrated, bioartificial nephron, including a Loop of Henle, distal tubule and collecting duct is provided. The exemplary device (and its component parts) includes topographical surfaces for renal cell growth, and cell growth regions that can be exposed to fluid shear stress (FSS) to stimulate renal cell growth patterns and cell function which more closely mimic cell growth patterns and function found in vivo. While various embodiments of a bioartificial Loop of Henle are described herein, it is understood that the topographical growth surfaces and FSS features used to pattern cells in the Loop of Henle can be applied to other structures of a bioartificial kidney, including but not limited to bioartificial distal tubules and collecting ducts. In addition, while the discussion below describes ridges and grooves, any of the surface topographies disclosed herein may be included in one or more regions of a bioartificial kidney to yield cell growth that will more closely mimic that of an in vivo system. Non-limiting exemplary topographies or topographical modifications include varying pitch of topographical features, varying the orientation of a topographical feature with respect to fluid flow (e.g., parallel to the direction of fluid flow, or perpendicular to the direction of fluid flow), and inclusion of any one or more of the topographies of the pit and post family. Additionally, transition surfaces can be included between different topographical regions, to allow a graded or gradual change from one cell arrangement, behavior and/or morphology to another.

As is known in the art, different regions of the kidney experience different shear stresses. Both flow rate and diameter influence shear stress, and both may change along any given region of a kidney, nephron or tubule. Without wishing to be bound by theory, it is thought that in general, the flow rate (volumetric flow) is higher "upstream," since the fluid is resorbed to tissues along the tubule. Accordingly, flow rate for a nephron, from highest to lowest, would likely be ordered as follows: proximal tubule, then descending limb loop of Henle, then ascending limb of loop of Henle, then distal tubule, followed by the start of the collecting duct. Shear likely follows the same trend as flow rate from high to low; however, as the diameter of a given region changes, the correlations between flow and shear may not be exact. Another factor to consider when evaluating flow and shear, in addition to variation in diameter, is the influence of smaller tributaries that feed into larger vessels. For example, the collecting duct builds in diameter, but the flow rate increases "downstream." This is because smaller tributaries feed into the larger the vessel downstream.

Accordingly, the bioartificial kidney can be configured to expose cells in any given region to experience a specific FSS or series of FSS, or FSS cycles (generally an "FSS profile"). That is, cells in a first region of the bioartificial kidney are exposed to first FSS profile, where as cells in other regions of the bioartificial kidney may be exposed to a different FSS profiles. For example, in some embodiments, FSS levels in one or more FSS profiles range from about 0.02-1.0 dyne/$cm^2$. In some embodiments, FSS levels of about 0.1 dyne/$cm^2$ or less are employed in one or more FSS profiles. In still other embodiments, FSS levels of about 0.01, 0.02, 0.05, 0.07, 0.09, 0.1, 0.2, 0.3, 0.4, 0.5, 0.6, 0.7, 0.8, 0.9, 1.0, 1.2, 1.4, 1.6, 1.8, 2.0, 3.0, 4.0, 5.0, 6.0, 7.0, 8.0, 9.0 or up to about 10.0 dyne/$cm^2$ are used in one or more FSS profiles. In some embodiments, FSS levels of 10.0 dyne/$cm^2$ or greater is used in one or more FSS profiles. In some embodiments, the FSS rate in a FSS profile is altered/fluctuated during cell growth to achieve the desired cellular alignment, cellular patterning and/or other desired cellular characteristics (e.g., altered expression of tight junction proteins, extracellular matrix proteins, desired cellular functions, etc.).

A. Integrated Device

In a kidney, blood is first filtered through glomeruli, and the filtrate flows out of the glomerulus and into the proximal tubule, then into the Loop of Henle, then into the distal tubule and collecting duct. According to one implementation, a biomimetic apparatus of the invention is used to replace the Loop of Henle, distal tubule, and collecting duct, supplying the functions of the glomerulus and proximal tubule. FIG. 10 shows a schematic of an illustrative integrated device according to this implementation. As shown, the device 100 of FIG. 10 includes a bioartificial loop 10 that mimics the function of the Loop of Henle, distal tubule 20 and collecting duct 30, all interconnected to replace their biological counterparts. Each of these structures can be provided with topographical features to specifically pattern cell growth therein. In addition, the different structures (e.g., the Loop of Henle, distal tubule and collecting duct) can be designed such that cells within the structures are exposed to fluid shear stress, thereby further patterning the cells, both positionally and functionally, within the structures.

As illustrated, the device 100 comprises a blood flow layer 200 and a filtrate layer 300, and a membrane positioned in between the two layers 200 and 300. The blood flow layer 200, as shown, includes a blood flow layer 210 of the loop 10, a blood flow layer 230 of the collecting duct 30 and a blood flow layer 220 of the distal tubule 20; the three component blood flow layers 210, 220, and 230 of the blood flow layer 200 lie in substantially one plane. In alternative embodiments, the component blood layers 210, 220, and 230 form a substantially three-dimensional network or lie in substantially two or more planes. The blood flow layer 200 further comprises microfluidic channels or microchannels formed therein, which allow blood flow from the blood inlet 110 into the device 100 and out of the device through the blood outlet 120.

As illustrated, the device 100 comprises a filtrate layer 300 also including three components, a filtrate layer 310 of the loop 10, a filtrate layer 330 of the collecting duct 30, and a filtrate layer 320 of the distal tubule 20. Similarly, these component filtrate layers may lie in the same plane or in multiple planes. Similarly, these component filtrate layers may form a substantially three-dimensional network. The filtrate layer 300 further comprises microfluidic channels or microchannels formed therein, which allow filtrate flow from the filtrate inlet 130 into the device 100 and out of the device through the filtrate outlet 140.

In certain embodiments involving three-dimensional microfluidic networks, vertical links or vertical pores are employed to put the different layers in the networks in fluid communication with each other. A "vertical link" or "vertical pore" generally refers to a partial or complete through hole that vertically connects one microchannel in one layer to at least another microchannel in the same or a second layer. Vertical links are generally substantially perpendicular to the layers or the microchannels which they connect. Hollow fibers can be incorporated into the devices and systems to form such vertical pores.

Also as illustrated, the device 100 comprises a membrane. The membrane includes three components, the membrane 410 of the loop 10, the membrane 420 of the distal tubule 20, and the membrane 430 of the collecting duct 30. Each of the component membranes 410, 420, 430, is positioned in between its respective component blood flow layer and component filtrate layer. As illustrated, the component membranes 410, 420, and 430 are separate from each other. In alternative embodiments, the component membranes 410, 420, and 430 may be part of a single piece of membrane.

As shown, the membrane and its components have an upper surface that is exposed to the blood flow layer 200, and a lower surface that is exposed to the filtrate layer 300.

In certain embodiments, the membrane and its components are semi-permeable. Preferably, the pore size of the membrane is smaller than the cell diameters such that cells are not able to pass through (i.e., a low permeability for animal cells), while low molecular weight nutrients and fluids can pass through (i.e. a high permeability for nutrients). Cell sizes vary but in general, they are in the range of microns. In certain embodiments, the membrane is made of a hemocompatible material. Preferably, the average membrane pore size is on a submicron-scale to ensure effective screening of the cells. Semi-permeable membranes include a wide array of different membrane types and morphologies, which can be classified as follows: (1) Track-etch membranes consisting of cylindrical through-holes in a dense polymer matrix, typically made by ion-etching; or (2) Fibrous membranes made by various deposition techniques of polymeric fibers. While these membranes do not have a well-defined pore topology, production methods have been sufficiently refined so that fibrous membranes have specific molecular weight cut-offs. Track-etch type membranes are preferred, as they limit the fluid motion in one dimension. Preferably, fluid motion is in the vertical direction. Fibrous membranes permit fluid motion both laterally and vertically.

Any suitable approach, including those known in the art and those described in the cited U.S. Patents and Patent Applications, such as U.S. Pat. Nos. 6,942,879; 6,455,311, and U.S. Patent Application Publication Nos. 20060136182, 20050238687, 20050202557, 20030003575, 20020182241, as well as other references, may be employed to provide suitable porous membranes.

Figure 12:
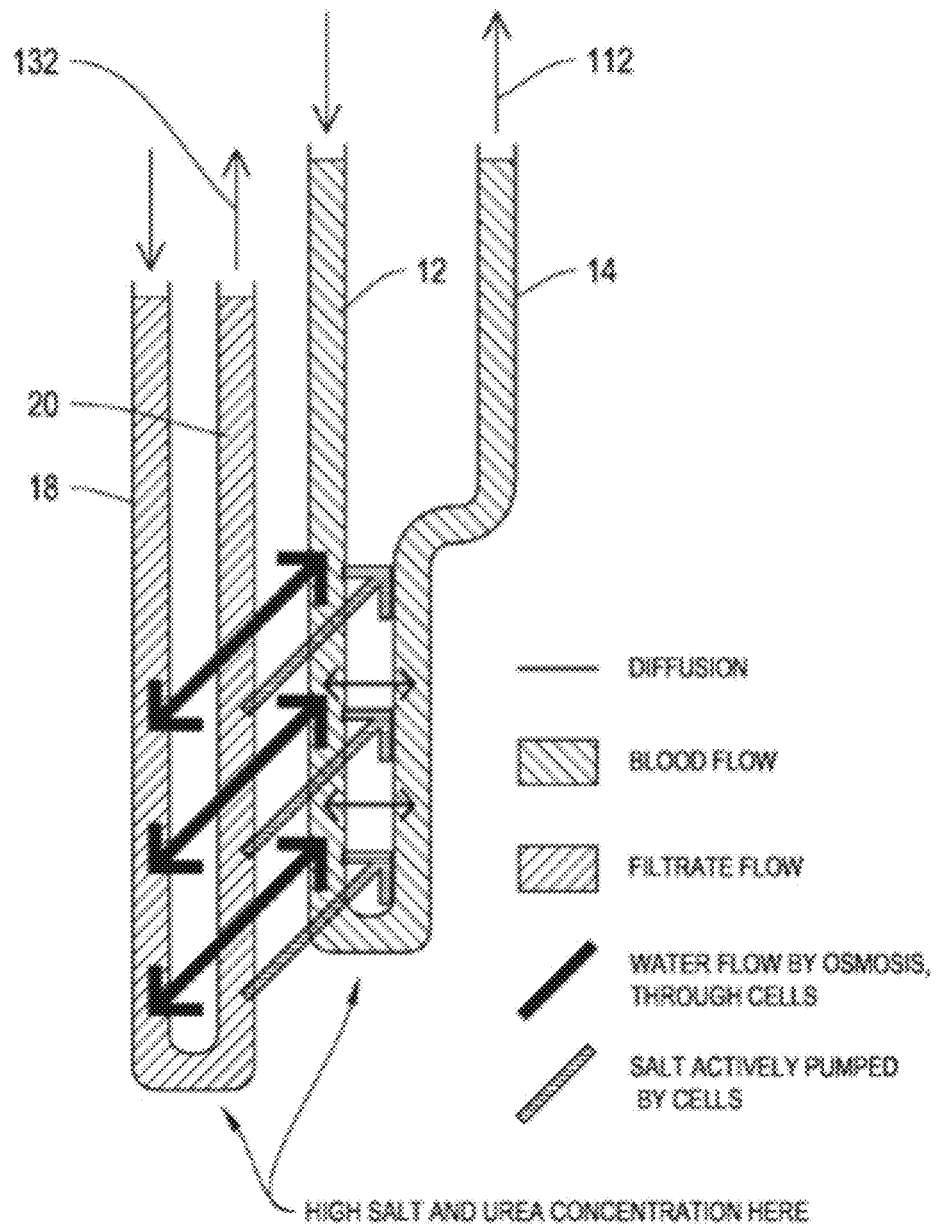
FIG. 12 is a schematic of flow behaviors in a microfabricated bioartificial Loop of Henle comprising topographical structures for stimulating patterned cell growth according to an illustrative embodiment of the invention.

B. Bioartificial Loop of Henle Comprising Topographical Surfaces and FSS Regions Stimulates Renal Cell Growth Patterns to More Closely Mimic In Vivo Systems 1. General Structure An essential function of the Loop of Henle is to create high concentrations of urea, salt, and other solutes. A bioartificial loop that mimics the function of the Loop of Henle according to an illustrative embodiment of the invention is depicted in FIG. 11. The illustrative bioartificial Loop of Henle shown in FIG. 11 (*and* also depicted in FIG. 10 as part of the assembled device) includes a substantially u-shaped microfluidic channel having a descending limb 18 and an ascending limb 20 formed in the corresponding filtrate layer 310 to carry filtrate flow from the filtrate inlet 130 through the outlet 132. In addition, the bioartificial loop 10 includes a bioartificial blood vessel also comprising a descending limb 12 and ascending limb 14 formed in the corresponding blood flow layer 210 to carry blood flow from the blood inlet 110 through the outlet 112. A porous medium 16 positioned between a substantial portion of the limbs 12 and 14 allows diffusion between the two limbs 12 and 14 of the blood flow layers. Communication between the two limbs 12 and 14 contributes to the countercurrent system of the blood flow layer 210 to create high-concentration blood at the tip 28 of the microchannel of the blood flow layer 210 as shown in FIG. 12.

Figure 13:
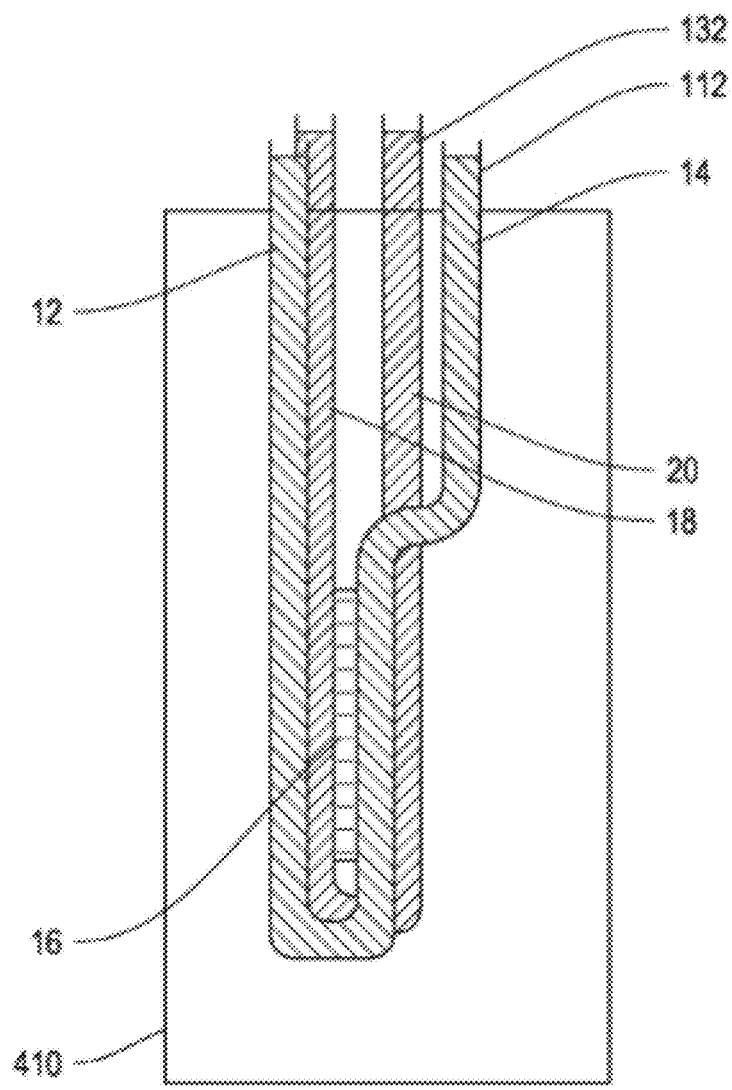
FIG. 13 is a schematic of assembled layers of a microfabricated bioartificial Loop of Henle comprising topographical structures for stimulating patterned cell growth according to an illustrative embodiment of the invention.

In an exemplary embodiment, a single bioartificial blood vessel is coupled with a substantially u-shaped tubule as shown in FIG. 13 through the loop membrane 410 to make the bioartificial Loop of Henle 10.

As shown in FIGS. 11 and 13, according to the illustrative embodiment, this bioartificial Loop of Henle 10 is formed on two microfabricated layers 210 and 310 separated by a water- and protein-permeable (porous) membrane 410. As shown in FIG. 12, glomelular filtrate circulates in one layer (filtrate layer 310) and blood in the other (blood flow layer 210).

Figure 14:
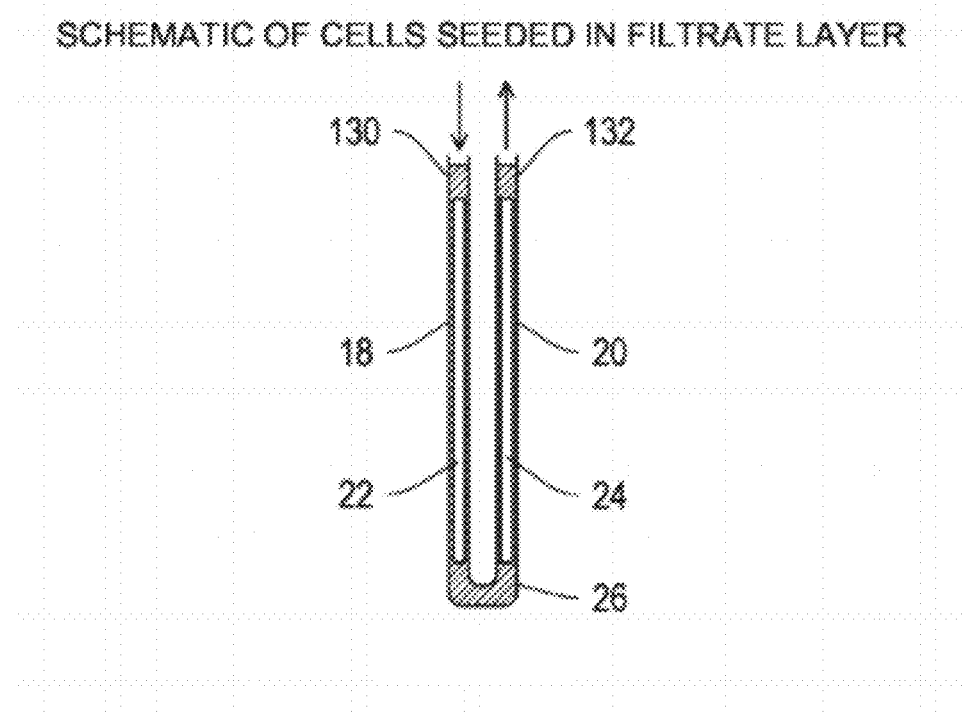
FIG. 14 is a schematic of cells seeded in a filtrate layer of the microfabricated bioartificial Loop of Henle of FIG. 10 and comprising topographical structures for stimulating patterned cell growth according to an illustrative embodiment of the invention.

The bioartificial loop 10, in particular, the substantially u-shaped microchannel in the filtrate layer 310 may further include a plurality of renal epithelial cells as shown in FIG. 14. The descending limb 18 includes or is lined with cells 22 that generally permit water to pass through and little else. The ascending limb 20 is lined with cells 24 that pump NaCl out of the tubule or microchannel and generally do not allow water to pass. These are also generally referred to as water-permissive or permeable and salt-pumping cells, respectively. According to one feature, the actions of pumping salt out of the ascending tubule and circulating flow by having correctly permeable walls of the microchannels creates a countercurrent multiplier. In such an arrangement, the concentration of solutes at the tip 26 of the u-shape becomes much higher than the concentration at the inlet 130 and outlet 132. In particular embodiments, the substantially u-shaped microchannel has different depths or diameters where the microchannel has a substantially cylindrical shape. For example, the ascending limb 20 may be thicker than the descending limb 18. In one exemplary embodiment, the ascending limb 20 has a substantially cylindrical shape and a diameter of about 60 microns, and the descending limb 18 has a substantially cylindrical shape and a diameter of about 12 microns.

The salt-pumping cells in a biological or natural Loop of Henle are thought to be typically less powerful than those found in the renal proximal tubule. According to one approach, cells pumping NaCl at 10-90% of the conventionally accepted rate of renal proximal tubule cells are selected to be included in the ascending limb 20 of the bioartificial loop 10. Thus, they pump $Na^+$ at a rate of $1.6 \times 10^{-6}$ mmol/s/cm$^2$ or higher.

2. Topographical Surfaces and FSS within the Ascending and Descending Limbs

Thus, according to one illustrative embodiment, an artificial Loop of Henle structure of the invention includes a microchannel with an ascending limb and descending limb, comprising one or more topographical surfaces for renal cell growth. In one non-limiting example, the surface comprises a ridge/groove topography. In a particular embodiment, ridges and groves are about 0.75 μm wide and 0.75 μm deep with about a 1.5 μm pitch. The skilled artisan will understand that alternative surface topography described herein may be structured in either or both limbs, resulting in modified or alternative cellular patterning.

In some embodiments, the topographical cell-growth surface is coated with an extracellular matrix protein, such as collagen IV, adsorbed to a self-assembled monolayer (SAM) comprising, e.g., hexadecanethiol molecules. Renal cells (e.g., HK-2 cells) are then seeded on the growth surface, and in some embodiments, cells are subject to FSS of 0.01-10.0 dyne/cm$^2$. Cells can be exposed to FSS during growth, after confluence, or both during growth and at cell confluence. Additionally or alternatively, FSS may be applied to the cells continually or periodically. In some embodiments, an FSS of 0.02-1.0 dyne/cm$^2$ is employed. In still other embodiments, an FSS of about 0.01, 0.02, 0.05, 0.07, 0.09, 0.1, 0.2, 0.3, 0.4, 0.5, 0.6, 0.7, 0.8, 0.9, 1.0, 1.2, 1.4, 1.6, 1.8, 2.0, 3.0, 4.0, 5.0, 6.0, 7.0, 8.0, 9.0 or 10.0 dyne/cm$^2$ is used. In some embodiments, the FSS rate is altered/fluctuated during cell growth to achieve the desired cellular alignment, cellular patterning and/or other desired cellular characteristics (e.g., altered expression of tight junction proteins, extracellular matrix proteins, desired cellular functions, etc.). As is known in the art, different regions of the nephron (e.g., different regions of the Loop of Henle, the collecting tubule, and the distal tubule) experience different shear stresses. Accordingly, the bioartificial kidney can be configured to expose cells in any given region to experience a specific FSS or series of FSS, or FSS cycles.

As shown in Example 1, renal cell growth under such conditions (i.e., on topographical substrate and under FSS) results in cells with enhanced alignment, adherence properties and/or tight junction properties at shear stress as low as 0.02 dyne/cm$^2$ and as high as 1.0 dyne/cm$^2$ when compared to cells grown on a blank, un-textured surface in the absence of FSS. Cells grown by methods of the present technology more closely mimic those found in the in vivo environment and are thus superior for use in bioartificial devices, such as artificial nephrons, or portions thereof, compared to cells grown under "standard" conditions (e.g., on a flat or un-textured surface and in the absence of FSS).

In the bioartificial Loop of Henle exemplified above, the ascending limb will thus be lined with cells that actively transport Na$^+$ at about 1.6×10$^-$ mmol/s/cm$^2$ and block other transport, and the descending limb will be lined with cells that allow transport of water and block or substantially block the transport of most, if not all, other species (including protein and other molecules in the filtrate). Because the cells will have been grown on a topographical surface and exposed to FSS, it is anticipated that the cellular patterning, adherence, and/or tight junction characteristics will influence not only the overall structure of the bioartificial device at the cellular level (see e.g., Example 1), but will also influence the function of the device. Cells will be encouraged, based on proximity to other cells and exposure to FSS, to function more like their in vivo counterparts. As such, cellular function will more closely mimic in vivo cell function.

As noted above, similar topographical features can be designed into the distal tubule and collecting duct, and renal cells in these structures can likewise be exposed to FSS to stimulate desired patterning.

EXAMPLES

The following examples are provided to more fully illustrate various embodiments of the present technology. These examples should in no way be construed as limiting the scope of the invention.

Example 1

Fluid Shear Stress Enhances Alignment of Cells to Topographic Patterns

A. Biomimetic Flow Apparatus

Figure 15:
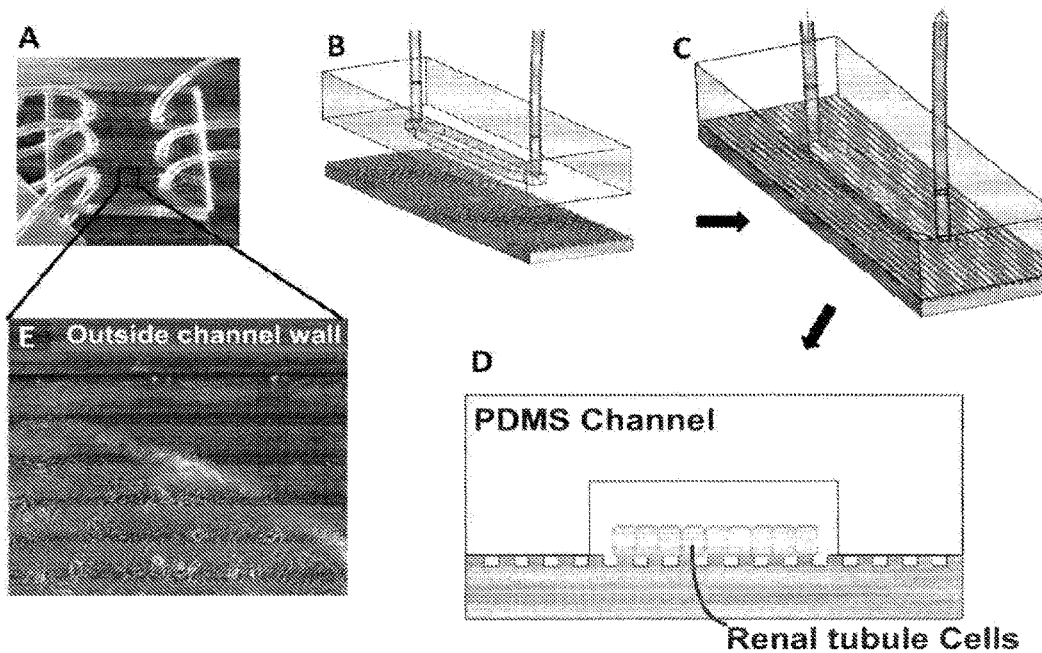
FIGS. 15A, 15B, 15C and 15D are photographs of an illustrative embodiment of a biomimetic flow apparatus of the invention.
FIG. 15E is a phase contrast image of cells within the channel adhered to the ECM-coating region.

A biomimetic flow apparatus of the present technology, comprising ridge/groove features was constructed. The structure of the flow apparatus is shown in FIG. 15 A-D. The flow apparatus included an array of fluidic channels to control fluid shear stress (FSS) and cell substrates with controlled surface properties. The disassembled (FIG. 15 B) and assembled (FIG. 15 C) apparatus includes two layers: micromolded channels and a topographically patterned substrate treated with ECM protein to cue cell adhesion and function. A cross-section of the apparatus illustrates a confluent layer of renal tubule cells within the microfluidic channel and adherent to the topographical substrate (FIG. 15 D). A phase contrast image of cells within the channel and adhered to the ECM-coated region (FIG. 15 E).

Figure 16:
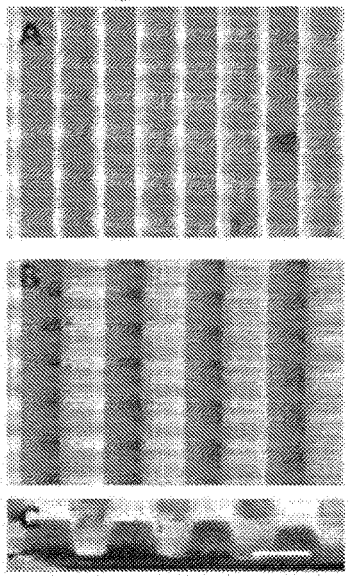
FIG. 16A is photograph of a nickel alloy mold used to fabricate a ridge/groove pattern surface in an illustrative embodiment of the invention.
FIG. 16B is a photograph of a polystyrene substrate in an illustrative embodiment of the invention.
FIG. 16C is a photograph of the edge profile of the polystyrene substrate shown in FIG. 16B.

Topographical features were hot embossed from a nickel alloy mold to a polystyrene substrate (FIGS. 16 A and B, respectively). The edge profile of the polystyrene substrate shows defined ridge/groove features (FIG. 16 C). Ridges and grooves are 0.75 μm wide and 0.75 μm deep with a 1.5 μm pitch. (Scale bar, 1 μm).

B. Flow-Induced Shear Stress Characterization

Characterization of the flow apparatus indicated that the channel design would provide known and uniform FSS to the cell adhesion area. Computational model simulations using COMSOL Multiphysics software predict a uniform shear stress over the cell adhesion area and most of the substrate surface area (data not shown). COMSOL simulations predict uniform shear stress across cell adhesion areas and most of the cell substrate. The shear stress distribution showed higher shear stress at the inlet and outlets of the channel which quickly develops to uniform shear stress in most of the channel including the circular cell adhesion area (data not shown). The shear stress profile plot was taken across the chamber floor, 12.5 mm from the inlet, and the plot indicates that shear stress varies less than 5% across the width of the channel (data not shown).

C. Cell Adhesion Area

The cell adhesion area includes collagen IV protein adsorbed to a self-assembled monolayer (SAM) of hexadecanethiol molecules. Briefly, the surface of a 2.5 mm-diameter, round polydimethylsiloxane (PDMS) stamp was painted with a 1 mM solution of hexadecanethiol (HDT in 200 proof ethanol). The solution was stamped onto the topographical surface (substrate) and firmly held for 30 seconds. After 30 seconds, the stamp was released. The surface was then back-flooded with 2 mM PEG (in 200 proof ethanol) for 2 hours. The PEG solution was removed via aspiration, and the surface was rinsed thoroughly with ethanol. The substrate was then incubated in a 30 μg/ml solution of collagen IV (in PBS) for 3 hours at room temperature. The collagen solution was removed by aspiration, and the substrate was rinsed thoroughly with PBS.

The SAM provides one exemplary model chemistry which provides consistent and characterizable adsorption of the extracellular matrix (ECM) protein, resulting in a repeatable ECM-based cue to the cells adhered. The SAM also enables chemical patterning of the surface through microcontact printing (μCP), which allows selective placement of cells in applications such as multiple phenotype co-culture and cell morphology influence. The collagen IV coating covers both the tops of ridges as well as surfaces within the grooves, as examined by SEM (data not shown). The combination of topographic patterning and μCP allows distinct control of both physical and chemical patterns to cue cells according to user-specified configurations.

Human renal proximal tubular epithelial cells (HK-2 cells; ATCC CRL-2190) were seeded on the functionalized ridge/groove surface of the apparatus and grown to confluence as follows. A cell suspension solution (containing media and HK-2s) was placed in a petri dish containing the topographically- and chemically-patterned substrate so that the initial seeding density was 300 cells/mm$^2$. Media was DMEM/F12 base supplemented with 0.5% FBS, 10 ng/mL hEGF, 5 μg/mL insulin, 0.5 μg/mL hydrocortisone, 0.5 μg/mL epinephrine, 6.5 ng/mL tri-iodothyronine, 10 μg/mL transferrin, 100 U/ml penicillin and 100 μg/mL streptomycin. Cells were placed in an incubator at 37° C. and 5% CO$_2$. Media was renewed every other day. Cells reached confluency within 3-4 days. Cells were then exposed to 2 hours of either 0, 0.02 or 1.0 dyne/cm2 FSS under the same conditions as described above.

D. Results

Results are shown in FIG. 17. Cells on textured substrates exhibited alignment to grooves, while cells on blank substrates did not (FIG. 17 A; the arrow indicates the direction of grooves on topographical substrates). The percentage of nuclei aligned to grooves within 10° increased significantly due to presence of grooves and FSS (FIG. 17 B). Regarding FIG. 17B: the first three bars represent cells grown on blank (non-textured) substrate and exposed to 0, 0.02 or 1.0 dyne/cm2 FSS. The last three bars represent cells grown on textured substrate and exposed to 0, 0.02 or 1.0 dyne/cm2 FSS. The presence of 1 dyne/cm2 FSS significantly increased alignment of nuclei for cells adherent to topographic substrates. Substantial improvement was also seen at 0.02 dyne/cm2 FSS. Data is presented as mean±standard deviation. *, P<0.001 versus blank, τ=0 samples, †, P<0.005 versus topographical, τ=0 substrates. (Scale bar, 30 μm).

Shear stress and topography both influence formation of tight junctions ("TJs") in HK-2 cells. Intensity of TJ formation was measured by quantifying ZO-1 intensities around perimeters of cells on blank and topographical substrates under FSS conditions. ZO-1 was visualized as follows. Cells were permeabilized with 0.5% Triton X-100 in PBS followed by blocking with 1% BSA for 30 minutes at room temperature. Cells were incubated with primary antibodies (ZO-1 594, Invitrogen) for 1 hour at room temperature. Cells were washed 3× in PBS and incubated with secondary antibody (goat anti-mouse IgG, Alexa Fluor 488, Invitrogen) for 1 hour at room temperature. Cells were washed 3× in PBS and coverslips were mounted to slides with ProLong Gold plus DAPI (Invitrogen) and allowed to cure overnight before microscopic analysis. Image analysis included measuring the intensity of the ZO-1 label using a conventional computer imaging program to determine fluorescent intensity of the ZO-1. The intensities were quantified for all borders of cells and the continuity of the junctions was quantified as well.

Results are shown in FIGS. 18 and 19. FIGS. 18 A and B shows representative images of ZO-1 expression for cells cultured on blank and topographical substrates and exposed to either 0, 0.02 or 1.0 dyne/cm2 FSS. With the addition of topography and FSS stimuli, morphology of the ZO-1 borders transitions from punctate to continuous. The arrow indicates the direction of ridge/groove topography. FIG. 19 A shows the intensity of ZO-1, integrated along cell perimeters and normalized by cell perimeter, quantified tight junction expression and distribution. The ZO-1 intensity increased significantly in cells cultured on topographical substrates compared to those on blank surfaces. Cells exposed to all levels of FSS on topographical substrates showed a significant increase in ZO-1 intensity compared to cells on topographical substrates exposed to τ=0 conditions. FIG. 19 C shows the standard deviation of ZO-1 intensity measured along cell perimeters and quantifies tight junction continuity. Standard deviation of ZO-1 intensity decreased for all topographical samples compared to cells on blank surfaces and was lowest for cell populations exposed to both topographical substrates and FSS. Cell populations on blank surfaces did not present ZO-1 intensity differences after two hours of FSS. Data is presented as mean±standard deviation. *, P<0.05 versus blank, τ=0 samples; **, P<0.001 versus blank, τ=0 samples; t, P<0.001 versus topographical τ=0 samples. (Scale bar, 15 μm).

The perimeters of cells, as defined by the ZO-1 TJs, transition to a higher intensity with more fluorescence signal as topography and FSS are applied. Overall fluorescent signal, as well as location of the fluorescent signal, indicates increased ZO-1 expression and translocation to cell perimeters. Standard deviation of the ZO-1 intensity around the cell perimeter serves as a quantifiable metric of TJ continuity. Lower standard deviations translate to a more continuous ZO-1 perimeter. Cell perimeters transition from a more punctuate morphology to a continuous morphology with the application of topography and FSS, as measured by ZO-1 intensity standard deviation. Taken together, increases in TJ intensity and continuity indicate a progression towards a quality barrier function for cells grown with topographical substrate and FSS exposure, and a move towards tubule-specific function. The enhancement of cell response to FSS on topographical substrates indicates the synergistic influence of these two physical stimuli. Cells cued by the biomimetic flow apparatus which exhibit high and continuous intensity of ZO-1-labeled TJs are likely poised to form a well-developed, highly functioning epithelial layer with the natural filtering behavior of the renal proximal tubule.

What is claimed is:

1. A bioartificial kidney comprising:
   a microfluidic flow channel comprising at least one topographical surface;
   an inlet in fluid connection with the flow channel for allowing fluid to flow into the flow channel; and
   renal cells seeded on the topographical surface as a confluent monolayer; wherein
   the topography of the surface of the flow channel comprises ridges parallel to a length of the microfluidic flow channel and having a width less than 5 μm and wherein the confluent monolayer of renal cells forms a substantially fluid-impermeable barrier.

2. The bioartificial kidney of claim 1, wherein the topography of the surface is configured to promote increased adhesion of cells in the cell layer to the at least one surface.

3. The bioartificial kidney of claim 1, further comprising a fluid source coupled to the flow channel via the inlet, wherein the fluid source is configured to flow a fluid through the flow channel and induce a shear stress upon the cell layer.

4. The bioartificial kidney of claim 3, wherein the flow channel is formed as part of one or more structures selected from the group consisting of a Loop of Henle, a collecting tubule and a distal tubule.

5. The bioartificial kidney of claim 3, wherein the fluid source is configured to flow the fluid at a flow rate that results in a level of shear stress on the cell layer that is less than or equal to about 10.0 dyne/cm2 in at least one region of the bioartificial kidney.

6. The bioartificial kidney of claim 3, wherein the fluid source is configured to flow the fluid at a flow rate that results in a level of shear stress on the cell layer that is less than or equal to about 1.0 dyne/cm2 in at least one region of the bioartificial kidney.

7. The bioartificial kidney of claim 3, wherein the fluid source is configured to flow the fluid at a flow rate that results in a level of shear stress on the cell layer that is less than or equal to about 0.1 dyne/cm2 in at least one region of the bioartificial kidney.

8. The bioartificial kidney of claim 3, wherein the fluid source is configured to flow the fluid at a flow rate that results in a level of shear stress on the cell layer that is about 0.02 dyne/cm2 in at least one region of the bioartificial kidney.

9. The bioartificial kidney of claim 3, wherein the flow channel is configured such that the fluid flows at a first flow rate in a first region of the bioartificial kidney and at a second flow rate in a second region of the bioartificial kidney.

10. The bioartificial kidney of claim 9, wherein the first flow rate results in a first level of shear stress on the cell layer in the first region, and wherein the second flow rate results in a second level of shear stress on the cell layer in the second region, and wherein the first and second levels of shear stress are different.

11. The bioartificial kidney of claim 9, wherein the bioartificial kidney comprises a Loop of Henle comprising an ascending limb and a descending limb, and wherein the first region is the ascending limb of the Loop of Henle, and the second region is the descending limb of the Loop of Henle.

12. The bioartificial kidney of claim 9, wherein the bioartificial kidney comprises a collecting duct, a distal tubule, and a Loop of Henle comprising an ascending limb and a descending limb, wherein the first region is in the Loop of Henle, and the second region is in one or more of a collecting duct and a distal tubule.

13. The bioartificial kidney of claim 1, further comprising a first and second surface, wherein the first surface of the flow channel has a first topography, and wherein the second surface of the flow channel has a second topography.

14. The bioartificial kidney of claim 13, wherein the bioartificial kidney comprises a Loop of Henle comprising an ascending limb and a descending limb, wherein the first surface is in the ascending limb of the Loop of Henle, and wherein the second surface is in the descending limb of the Loop of Henle.

15. The bioartificial kidney of claim 13, wherein the bioartificial kidney comprises a collecting duct, a distal tubule, and a Loop of Henle comprising an ascending limb and a descending limb wherein the first surface is in the Loop of Henle, and wherein the second surface is in one or more of a collecting duct and a distal tubule.

16. The bioartificial kidney of claim 13, further comprising a transition topography surface between the first and second surface.

17. The bioartificial kidney of claim 13, wherein the topography of the first surface comprises ridges with a first pitch, and the topography of the second surface comprises ridges with a second pitch.

18. The bioartificial kidney of claim 13, wherein the topography of the first surface comprises ridges in a first orientation with respect to fluid flow, and the topography of the second surface comprises ridges in a second orientation with respect to fluid flow.

19. The bioartificial kidney of claim 13, wherein the first topography comprises ridges, and the second topography comprises one or more topographies of the pit or post families.

20. The bioartificial kidney of claim 1, further comprising a cytophilic substance disposed on a portion of a substrate for growing the cell layer in the portion of the substrate, and wherein the portion of the substrate forms a surface of the flow channel.

21. The bioartificial kidney of claim 20, wherein the cytophilic substance comprises a collagen protein.

22. The bioartificial kidney of claim 1, wherein the surface topography is configured to cause the arrangement, behavior, or morphology of the cell layer to replicate an arrangement, behavior, or morphology of cells in a kidney.

23. The bioartificial kidney of claim 1, further comprising at least a second flow channel having at least one surface of the second flow channel having a topography formed therein.

24. The bioartificial kidney of claim 23, wherein the first flow channel is separated from the second flow channel by a membrane.

25. The bioartificial kidney of claim 23, wherein the first flow channel is seeded with renal epithelial cells.

26. The bioartificial kidney of claim 23, wherein the second flow channel is seeded with vascular epithelial cells.

27. The bioartificial kidney of claim 23, wherein the first flow channel comprises a blood flow layer, and the second flow channel comprises a filtrate layer.

28. The bioartificial kidney of claim 23, wherein at least one surface of the first channel and includes a different surface topography than a corresponding surface in the second channel.

29. The bioartificial kidney of claim 28, wherein the surface topography in the first channel comprises a different pitch or shape than the surface topography in the second channel.

30. The bioartificial kidney of claim 23, further comprising a first fluid source for flowing a fluid through the first flow channel and the second flow channel, wherein the fluid induces a first shear stress upon the cell layer in the first channel and a second shear stress upon the cell layer in the second channel.

31. The bioartificial kidney of claim 30, wherein the first shear stress is different than the second shear stress.

32. The bioartificial kidney of claim 1, wherein the renal cells comprise one or more cell types selected from the group consisting of proximal tubule cells, renal proximal tubule epithelial cells, Madin-Darby canine kidney cells, primary inner medullary collecting duct cells, primary proximal tubule cells, embryonic stem-cells, adult stem-cells, induced pluripotent stem cells and endothelial cells.

33. A bioartificial kidney comprising:
a microfluidic flow channel comprising at least one topographical surface;
an inlet in fluid connection with the flow channel for allowing fluid to flow into the flow channel; and
renal cells seeded on the topographical surface;
wherein the topography of the surface of the flow channel comprises ridges parallel to a length of the microfluidic flow channel and having a width of about 1 µm or about 3 µm and is selected to cause the renal cells to form a cell layer disposed on the surface to achieve an arrangement, behavior, or morphology determined at least in part by the topography of the at least one surface.

\* \* \* \* \*